US005695752A

United States Patent [19]
Rosen et al.

[11] Patent Number: 5,695,752
[45] Date of Patent: Dec. 9, 1997

[54] TREATING INFLAMMATION VIA THE ADMINISTRATION OF SPECIFIC SULFATASE ENZYMES AND/OR SULFATION INHIBITOR

[75] Inventors: Steven D. Rosen; Stefan Hemmerich, both of San Francisco, Calif.; Yasuyuki Imai, Tokyo, Japan

[73] Assignee: The Regents of the University of California, Oakland, Calif.

[21] Appl. No.: 496,857

[22] Filed: Jun. 30, 1995

Related U.S. Application Data

[63] Continuation of Ser. No. 214,947, Mar. 16, 1994, abandoned, which is a continuation-in-part of Ser. No. 943,817, Sep. 11, 1992, abandoned, and Ser. No. 155,947, Nov. 19, 1993, abandoned.

[51] Int. Cl.$^6$ .......................... A61K 38/47; A61K 38/46; A61K 38/43; C12N 9/24
[52] U.S. Cl. ................... 424/94.61; 424/94.6; 424/94.1; 435/196; 435/200
[58] Field of Search .................... 424/94.61, 94.6, 424/94.1; 435/196, 200

[56] References Cited

U.S. PATENT DOCUMENTS

| 4,163,783 | 8/1979 | Klein et al. | 424/245 |
|---|---|---|---|
| 4,370,325 | 1/1983 | Packman | 424/245 |
| 4,849,513 | 7/1989 | Smith et al. | 536/27 |
| 5,013,724 | 5/1991 | Petitou et al. | 514/54 |
| 5,143,172 | 9/1992 | Brandley et al. | 424/1.1 |

FOREIGN PATENT DOCUMENTS

| WO 92/02527 | 2/1992 | WIPO . |
|---|---|---|
| WO92/02527 | 2/1992 | WIPO . |

OTHER PUBLICATIONS

Roberton et al, Biochem. J. 293:683–689 (1993).
Tomatsu et al, Biochem. Biophys. Res. Comm. 181(2):677–683 (1991).
Robertson et al, Biochem. Biophys. Res. Comm. 157(1): 218–224 (1988).
Glabe et al., "Preparation and Properties of Fluorescent Polysaccharides", Anal. Biochem., 130:287–294 (1983).
Kishimoto et al., "Identification of a human peripheral lymph node homing receptor: A rapidly down-regulated adhesion molecule", Proc. Natl. Acad. Sci. USA, 87:2244–2248 (1990).
Lasky, L.A., "Lectin Cell Adhesion Molecules (LEC-CAMs): A New Family of Cell Adhesion Proteins Involved With Inflammation", J. Cell Biochem., 45:139–146 (1991).
Rosen et al., "L-Selectin: A Lectin-Like Leukocyte Adhesion Protein", Trends in Glycoscience and Glycotechnology, 4:1–13 (1992).
Springer, T., "Adhesion Receptors of the Immune System", Nature, 346:425–434 (1990).
Stoolman et al., "Phosphomannosyl Receptors May Participate in the Adhesion Interaction between Lymphocytes and High Endothelial Venules", J. Cell Biol., 99:1535–1540 (1984).
Willenborg et al., "Phosphosugars are potent inhibitors of central nervous system inflammation", Faseb. J., 3:1968–1971 (1989).
Willenborg et al., "Inhibition of Allergic Encephalomyeltis in Rats by Treatment With Sulfated Polysaccharides", J. Immunol., 140:3401–3405 (1988).
Brandley, et al., "Cell–Surface Carbohydrates in Cell Recognition and Response," J. Leuk. Biol., (1986) 40:97–111.
Sharon, et al., "Lectins as Cell Recognition Molecules," Science, (1989) 246:227–234.
Dodd, et al., "Lactoseries Carbohydrates Specify Subsets of Dorsal Root Ganglion Neurons Projecting to the Superficial Dorsal Horn of Rat Spinal Cord," J. Neurosci., (1985) 5(12):3278–3294.
Regan, et al., "Selective Expression of Endogenous Lactose–binding Lectins and Lactoseries Glycoconjugates in Subsets of Rat Sensory Neurons," Proc. Natl. Acad. Sci. USA, (1986) 83:2248–2252.
Constantine–Paton, et al., "A Cell Surface Molecule Distributed in a Dorsoventral Gradient in the Perinatal Rat Retina," Nature, (1986) 324:459–462.
Tiemeyer, et al., "Ganglioside–specific Binding Protein on Rat Brain Membranes," J. Bio. Chem., (1989) 264(3):1671–1681.
Bevilacqua, et al., "Identification of an Inducible Endothelial–Leukocyte Adhesion Molecule," Proc. Natl. Acad. Sci. USA, (1987) 84:9238–9242.
Fukuda, et al., "Structure of a Novel Sialylated Fucosyl Lacto–N–nor–hexaosylceramide Isolated from Chronic Myelogenous Leukemia Cells," J. Biol. Chem., (1986) 261(5):2376–2383.

(List continued on next page.)

Primary Examiner—Leon B. Lankford, Jr.
Assistant Examiner—Francisco C. Prats
Attorney, Agent, or Firm—Karl Bozicevic; Bret Field; Bozicevic & Reed

[57] ABSTRACT

Compositions are administered to a patient (preferably by injection and locally) to treat a variety of conditions including inflammation associated with trauma and with certain aspects of diseases such as rheumatoid arthritis, psoriasis, insulin-dependent diabetes, cutaneous lymphomas, duodenal ulcer, chronic proctitis, lymphocytic thyroidiris, hemorphagic shock, reperfusion injury during transplantation and multiple sclerosis. The compositions are pharmaceutically acceptable injectable formulations which include an active component in a pharmaceutically acceptable carrier. The active component is a chlorate or selenate which inhibits the natural biochemical sulfation process and/or a sulfatase enzyme which removes a sulfate from a specific position of a saccharide molecule which makes up a part of a natural ligand for L-selectin. Removal of the sulfate from the ligand hinders the ability of the ligand to bind to its natural receptor (i.e. L-selectin) and thereby hinders a biochemical chain of events which results in inflammation.

6 Claims, 2 Drawing Sheets

OTHER PUBLICATIONS

Magnani, et al., "A Monoclonal Antibody–defined Antigen Associated with Gastrointestinal Cancer is a Ganglioside Containing Sialylated Lacto–N–fucopentaose II," *J. Biol. Chem.*, (1982) 257(23):14365–14369.

Hakomori, et al., "Human Cancer–Associated Gangliosides Defined by a Monoclonal Antibody (IB9) Directed to Sialosylα2→6 Galactosyl Residue: A Preliminary Note," *Biochem. and Biophys. Res. Comm.*, (1983) 113(3):791–798.

Fukushi, et al., "Localization and Alteration of Mono–, DI–, and Trifucosyl α1→3 Type 2 Chain Structures During Human Embryogenesis and in Human Cancer," *J. Exp. Med.*, (1984) 159:506–520.

Geng, et al., "Rapid Neutrophil Adhesion to Activated Endothelium Mediated by GMP–140," *Nature*, (1990) 343:757–760.

Johnston, et al., "Cloning of GMP–140, a Granule Membrane Protein of Platelets and Endothelium: Sequence Similarity to Proteins Involved in Cell Adhesion and Inflammation," *Cell*, (1989) 56:1033–1044.

Geoffroy, et al., "Demonstration that a Lectin–like Receptor ($gp90^{MEL}$) Directly Mediates Adhesion of Lymphocytes to High Endothelial Venules of Lymph Nodes," *J. Cell Biol.*, (1989) 109:2463–2469.

Lasky, et al., "Cloning of a Lymphocyte Homing Receptor Reveals a Lectin Domain," *Cell*, (1989) 56:1045–1055.

Bevilacqua, et al., "Endothelial Leukocyte Adhesion Molecule 1: An Inducible Receptor for Neutrophils Related to Complement Regulatory Proteins and Lectins," *Science*, (1989) 243:1160–1165.

Watson, et al., "Neutrophil Influx into an Inflammatory Site Inhibited by a Soluble Homing Receptor–IgG Chimaera," *Nature*, (1991) 349:164–167.

Spertini, et al., "Regulation of Leukocyte Migration by Activation of the Leukocyte Adhesion Molecule–1 (LAM–1) Selectin," *Nature*, (1991) 349:691–694.

Imai, et al., "Direct Demonstration of the Lectin Activity of $gp90^{MEL}$, a Lymphocyte Homing Receptor," *J. Cell Biol.*, (1990) 111:1225–1232.

Imai, et al., "Identification of a Carbohydrate–based Endothelial Ligand for a Lymphocyte Homing Receptor," *J. Cell Biol.*, (1991) 113(5):1213–1221.

Lerouge, et al., "Symbiotic Host–specificity of *Rhizobium meliloti* is Determined by a Sulphated and Acylated Glucosamine Oligosaccharide Signal," *Nature*, (1990) 344:781–784.

Fiete, et al., "A Hepatic Reticuloendothelial Cell Receptor Specific for $SO_4$–4GalNAcβ1,4GlcNAcβ1,2Manα That Mediates Rapid Clearance of Lutropin," *Cell*, (1991) 67:1103–1110.

Baeuerle, et al., "Chlorate–A Potent Inhibitor of Protein Sulfation in Intact Cells," *Biochem. and Biophys. Res. Comm.*, (1986) 141(2):870–877.

Gallatin, et al., "A Cell–Surface Molecule Involved in Organ–Specific Homing of Lymphocytes," *Nature*, (1983) 304:30–34.

Stoolman, "Adhesion Molecules Controlling Lymphocyte Migration," *Cell*, (1989) 56:907–910.

Yednock, et al., "Phosphomannosyl–derivatized Beads Detect a Receptor Involved in Lymphocyte Homing," *J. Cell Biol.*, (1987) 104:713–723.

Yednock, et al., "Receptors Involved in Lymphocyte Homing: Relationship Between a Carbohydrate–binding Receptor and the MEL–14 Antigen," *J. Cell Biol.*, (1987) 104:725–731.

Bevilacqua, et al., "Selectins: A Family of Adhesion Receptors," *Cell*, (1991) 67:233.

Lasky, et al., "An Endothelial Ligand for L–Selectin Is A Novel Mucin–like Molecule," *Cell*, (1992) 69:927–938.

Rosen, et al., "Involvement of Sialic Acid on Endothelial Cells in Organ–Specific Lymphocyte Recirculation," *Science*, (1985) 228:1005–1007.

Imai, et al., "Further Characterization of the Interaction Between L–selectin and its Endothelial Ligands," *Glycobiology*, (1992) 2(4):373–381.

Siegelman, et al., "Mouse Lymph Node Homing Receptor cDNA Clone Encodes a Glycoprotein Revealing Tandem Interaction Domains," *Science*, (1989) 243:1165–1172.

Tedder, et al., "Isolation and Chromosomal Localization of cDNAs Encoding a Noval Human Lymphocyte Cell Surface Molecule, LAM–1," *J. Exp. Med.*, (1989) 170:123–133.

Camerini, et al., "Leu–8/TQ1 is the human equivalent of the Mel–14 lymph node homing receptor," *Nature*, (1989) 342:78–82.

Stoolman, et al., "Possible Role for Cell–surface Carbohydrate–binding Molecules in Lymphocyte Recirculation," *J. Cell Biol.*, (1983) 96:722–729.

Berg, et al., "The Human Peripheral Lymph Node Vascular Addressin is a Ligand for LECAM–1, the Peripheral Lymph Node Homing Receptor," *J. Cell Biol.*, (1991) 114(2):343–349.

Streeter, et al., "Immunohistologic and Functional Characterization of a Vascular Addressin Involved in Lymphocyte Homing into Peripheral Lymph Nodes," *J. Cell Biol.*, (1988) 107:1853–1862.

Rapraeger, et al., "Requirement of Heparan Sulfate for bFGF–Mediated Fibroblast Growth and Myoblast Differentiation," *Science*, (1991) 252:1705–1708.

Watson, et al., "A Homing Receptor–IgG Chimera as a Probe for Adhesive Ligands of Lymph Node High Endothelial Venules," *J. Cell Biol.*, (1990) 110:2221–2229.

Fiete, et al., "A Hepatic Reticuloendothelial Cell Receptor Specific for $SO_4$–4GalNAcβ1,4GlcNAcβ1,2Manα That Mediates Rapid Clearance of Lutropin," *Cell*, (1991) 67:1103–1110.

Roche, et al., "Molecular Basis of Symbiotic Host Specificity in *Rhizobium meliloti*: nodH and nodPQ Genes Encode the Sulfation of Lipo–Oligosaccharide Signals," *Cell*, (1991) 67:1131–1143.

Kjellén, et al., "Proteoglycans: Structures and Interactions," *Ann. Rev. Biochem.*, (1991) 60:443–475.

Lowe, et al., "ELAM–1–Dependent Cell Adhesion to Vascular Endothelium Determined by a Transfected Human Fucosyltransferase cDNA," *Cell*, (1990) 63.:475–484.

Phillips, et al., "ELAM–1 Mediates Cell Adhesion by Recognition of a Carbohydrate Ligand, Sialyl–Le$^x$," *Science*, (1990) 250:1130–1132.

Walz, et al., "Recognition by ELAM–1 of the Sialyl–Le$^x$ Determinant on Myeloid and Tumor Cells," *Science*, (1990) 250:1132–1135.

Tiemeyer, et al., "Carbohydrate ligands for endothelial–leukocyte adhesion molecule 1," *Proc. Natl. Acad. Sci. USA*, (1991) 88:1138–1142.

Polley, et al., "CD62 and Endothelial Cell–leukocyte Adhesion Molecule 1 (ELAM–1) Recognize the Same Carbohydrate Ligand, Sialyl–Lewis x," *Proc. Natl. Acad. Sci. USA*, (1991) 88:6224–6228.

Foxall, et al., "The Three Members of the Selectin Receptor Family Recognize a Common Carbohydrate Epitope, the Sialyl Lewis$^x$ Oligosaccharide," *J. Cell. Biol.*, (1992) 117(4):895–902.

Imai, Y. et al., "Sulphation Requirement for GlyCAM–1, an Endothelial Ligand for L–Selectin," *Nature* (1993) 361:555–557.

"Potassium Chlorate," *Martindale, The Extra Pharmacopoeia* Micromedex, Inc., vol. 78.

"Sodium Chlorate," *Martindale, The Extra Pharmacopoeia* Micromedex, Inc., vol. 78.

"Pastilles M.B.C.," *CD–ROM Vidal*, O.V.P.—editions du Vidal, Paris, 1992.

"Gargarisma" *Rote Liste*, Budesverband der Pharmazeutischen Industrie E.V., Edition Cantor, Aulendorf, 1992.

Lasky, L.A., "Lectin Cell Adhesion Molecules (LEC–CAMs): A New Family of Cell Adhesion Proteins Involved with Inflammation" *J. Cell. Biochem.* (1991) 45(2):139–146.

TREATING INFLAMMATION VIA THE ADMINISTRATION OF SPECIFIC SULFATASE ENZYMES AND/OR SULFATION INHIBITOR

CROSS-REFERENCES

This application is a continuation of U.S. patent application Ser. No. 08/214,947, filed Mar. 16, 1994, now abandoned, which is a continuation-in-part of earlier filed U.S. application Ser. No. 07/943,817, filed Sep. 11, 1992, now abandoned, and earlier filed U.S. application Ser. No. 08/155,947, filed Nov. 19, 1993, now abandoned, all of which applications are incorporated herein by reference and to which applications we claim priority under 35 U.S.C. § 120.

GOVERNMENT RIGHTS

The United States Government may have certain rights in this application pursuant to Grant No. GM-23547 awarded by the National Institute of Health.

FIELD OF THE INVENTION

The present invention relates generally to treating inflammation by preventing the metabolic addition of a sulfate to a natural ligand and/or the removal of a sulfate moiety from a specific position on a natural ligand to thereby hinder the attachment of the ligand to a receptor. More specifically, the invention relates to locally administering compounds such as non-toxic chlorates which metabolically prevent the addition of a sulfate moiety to a selectin ligand and/or administering specific sulfatase compounds which remove sulfate moieties resulting in desirable effects for alleviation of inflammation.

BACKGROUND OF THE INVENTION

There have been a number of research efforts investigating the role of carbohydrates in physiologically relevant recognition. (See Brandley, B. K., and Schnaar, R. L., *J. Leuk. Biol.* (1986) 40:97; and Sharon, N., and Lis, H., *Science* (1989) 246:227). Oligosaccharides are well positioned to act as recognition molecules due to their cell surface location and structural diversity. Many oligosaccharide structures can be created through the differential activities of a smaller number of glycosyltransferases. Their diverse structures, then, can be generated with relatively few gene products, suggesting a plausible mechanism for establishing the information necessary to direct a wide range of cell-cell interactions. Examples of differential expression of cell surface carbohydrates and putative carbohydrate binding proteins (lectins) on interacting cells have been described (see Dodd, J., and Jessel, T. M., *J. Neurosci.* (1985) 5:3278; Regan, L. J., et al., *Proc. Natl. Acad. Sci. USA* (1986) 83:2248; Constantine-Paton, M., et al., *Nature* (1986) 324:459; and Tiemeyer, M., et al., *J. Biol. Chem.* (1989) 263:1671).

Adhesion of circulating leukocytes to stimulated vascular endothelium is a primary event of the inflammatory response. Several receptors have been implicated in this interaction, including a family of putative lectins called selectins that includes L-selectin, LAM-1 (gp90$^{MEL}$, Leu8), P-selectin (GMP-140 (PADGEM, CD62) and E-selectin (ELAM-1) (Gong, J.-G., et al., *Nature* (1990) 343:757; Johnston, G. I., et al., *Cell* (1989) 56:1033; Geoffroy, J. S., and Rosen, S. D., *J. Cell Biol.* (1989) 109:2463; Lasky, L. A., et al., *Cell* (1989) 56:1045). All three of the presently known selectins have been shown to recognize carbohydrates (see Lasky, *Science*, 258:964–969, 1992). Endogenous ligands for these receptors are being identified.

E-selectin or ELAM-1 is interesting because of its transient expression on endothelial cells in response to IL-1 or TNF (Bevilacqua, M. P., et al., *Science* (1989) 243:1160). The time course of this induced expression (2–8 h) suggests a role for this receptor in initial neutrophil extravasation in response to infection and injury. Furthermore, Bevilacqua et al. (see Bevilacqua, M. P., et al., *Proc. Natl. Acad. Sci. USA* (1987) 84:9238) have demonstrated that human neutrophils or HL-60 cells will adhere to COS cells transfected with a plasmid containing a cDNA encoding the ELAM-1 receptor.

Recently, several different groups have published papers regarding E-selectin or ELAM-1 ligands which are also referred to as E-selectin ligands. Lowe et al. (1990) demonstrated a positive correlation between the E-selectin dependent adhesion of HL-60 cell variants and transfected cell lines, with their expression of the sialyl Lewis X (sLe$^x$) oligosaccharide, Neu NAc α2-3Gal-β1-4(Fuc α1-3)-GlcNAc and generally shown more specifically as Siaα2-3Galβ1-4[Fucα1-3]GlcNAc. By transfecting cells with plasmids containing an α(1,3/1,4) fucosyltransferase, they were able to convert non-myeloid COS or CHO lines into sLe$^x$-positive cells that bind in an E-selectin dependent manner. Attempts to block E-selectin dependent adhesion using anti-sLe$^x$ antibodies were uninterpretable due to the agglutination of the test cells by the antibody. They conclude that one or more members of a family of oligosaccharides consisting of sialylated, fucosylated, lactosaminoglycans are the ligands for the lectin domain of E-selectin. Phillips et al. (1990) used antibodies with reported specificity for sLe$^x$ to inhibit the E-selectin dependent adhesion of HL-60 or LEC11 CHO cells to activated endothelial cells. Liposomes containing difucosylated glycolipids with terminal sLe$^x$ structures inhibited adhesion, while those containing non-sialylated Lex structures were partially inhibitory. Walz et al. (1990) were able to inhibit the binding of a E-selectin-IgG chimera to HL-60 cells with a monoclonal antibody directed against sLe$^x$ or by glycoproteins with the sLe$^x$ structure, but could not demonstrate inhibition with CD65 or CD15 antibodies. Both groups concluded that the sLe$^x$ structure is the ligand for E-selectin.

Information regarding the DNA sequences encoding endothelial cell-leukocyte adhesion molecules are disclosed in PCT published application WO90/13300 published Nov. 15, 1990. The PCT publication cites numerous articles which may be related to endothelial cell-leukocyte adhesion molecules. The PCT publication claims methods of identifying E-selectin ligands, as well as methods of inhibiting adhesion between leukocytes and endothelial cells using such ligands and specifically refers to MILAs which are described as molecules involved in leukocyte adhesion to endothelial cells.

L-selectin or LECAM-1 is interesting because of its involvement in lymphocytic and neutrophil influx (Watson et al., *Nature*, 349:164–167 (1991)). It was expressed in chronic lymphocytic leukemia cells which bind to HEV (see Spertini et al., *Nature*, 349:691–694 (1991)). It is believed that HEV-like structures at sites of chronic inflammation are associated with the symptoms of disease such as rheumatoid arthritis, psoriasis, and multiple sclerosis.

A broad range of E-selectin ligands are disclosed in PCT/US91/05416 published as WO 92/02527 (published 20 Feb. 1992) to Brandley et al. and in PCT/US90/02357 published as WO 90/13300 (published 15 Nov. 1990) to Hession et al. both of which are incorporated herein by reference in their entirety and specifically to disclose oligosaccharide structures which reportedly act as E-selectin and L-selectin ligands.

The selectins are a family of three cell-cell adhesion proteins that mediate various leukocyte-endothelial adhesion events (reviewed in Lasky, L. A., Science, 258:964–969 (1992); McEver, R. P., Curr. Opin. Cell Biol., 4:840–849 (1992); Bevilacqua, M. P., and Nelson, R. M., J. Clin. Invest., 91:379–387 (1993); Rosen, S. D., Semin. in Immunol., 5:237–249 (1993). L-selectin is expressed on the surface of leukocytes and participates in the homing of blood borne-lymphocytes to peripheral lymph nodes (Gallatin, W. M., Weissman, I. L., and Butcher, E. C., Nature, 303:30–34 (1983); Geoffroy, J. S., and Rosen, S. D., J. Cell Biol., 109:2463–2469 (1989)) by mediating attachment to the specialized endothelial lining cells of high endothelial venules (HEV). L-selectin is also involved in the rolling interaction of neutrophils with venular endothelium at certain sites of acute inflammation (Lewinsohn et al., J. Immunol., 138:4313–4321 (1987); Ley, K., Gaehtgens, P., Fennie, C., Singer, M. S., Lasky, L. A., and Rosen, S. D., Blood, 77:2553–2555 (1991); Von Adrian, U., Chambers, J. D., McEvoy, L. M., Bargatze, R. F., Arfors, K. E., and Butcher, E. C., Proc. Natl. Acad. Sci. USA, 88:7538–7542 (1991)), an essential step for the ultimate extravasation of the leukocyte. The other two selectins, E- and P-, are expressed on endothelial cells where they mediate attachment to neutrophils, monocytes and specific subsets of lymphocytes. L-selectin participates in the entry of lymphocytes and monocytes into sites of chronic inflammation (Dawson et al., Eur. J. Immunol., 22:1647–1650 (1992), and Spertini et al., J. Exp. Med., 175:1789–1792 (1992)). The selectins perform their adhesive functions by virtue of C-type lectin domains at their amino termini (Drickamer, K., J. Biol. Chem., 263:9557–9560 (1988)). Reflecting a high degree of sequence similarity among these domains (60–70%), the biological ligands for L-selectin on HEV and for E- and P-selectin on leukocytes share a requirement for sialic acid (reviewed in Varki, A. Curr. Opin. Cell Biol., 4:257–266 (1992)). Moreover, each selectin is capable of recognizing sialyl Lewis X [sLe$^x$, i.e., NeuSAC$\alpha$2→3Gal$\beta$1→4(Fuc$\alpha$1→3)/GlcNAc] and related structures (reviewed in Stoolman, L. M., Cell Surface Carbohydrates and Cell Development, pp. 71–97 (1992) (M. Fukuda, ed.) CRC Press, Boca Raton, Fla.), although inhibition studies indicate that these compounds have a low binding affinity. L-selectin or LECAM-1, a lectin-like receptor bearing a calcium-type domain, mediates the attachment of lymphocytes to high endothelial venules (HEV) of lymph nodes (Gallatin et al., Nature, 303:30–34 (1983); Lasky, L. A., Science, 258:964–969 (1992); and Bevilacqua et al., J. Clin. Invest., 91:370–387 (1993)). There is evidence, based on the use of carbohydrate-specific antibodies, that sLe$^x$-related structures are present in the actual biological ligands of the selectins (Phillips, M. L., Nudelman, E., Gaeta, F., Perez, M., Singhal, A. K., Hakomori, S., and Paulson, J. C., Science, 250:1130–1132 (1990); Walz, G., Aruffo, A., Kolanus, W., Bevilacqua, M., and Seed, B., Science, 250:1132–1135 (1990); Polley, M. J., Phillips, M. L., Wayher, E., Nudelman, E., Singhal, A. K., Hakomori, S., and Paulson, J. C., Proc. Natl. Acad. Sci. USA, 88:6224–6228 (1991); Berg, E. L., Yoshino, T., Rott, L. S., Robinson, M. K., Warnock, R. A., Kishimoto, T. K., Picker, L. J., and Butcher, E. C., J. Exp. Med., 174:1461–1466 (1991); Sawada, M., Takada, A., Ohwaki, I., Takahashi, N., Tateno, H., Sakamoto, J., and Kannagi, R., Biochem. Biophys. Res. Commun., 193:337–347 (1993); Nogard, K. E., Moore, K. L., Diaz, S., Stults, N. L., Ushiyama, S., McEver, R. P., Cummings, R. D., and Varki, A., J. Biol. Chem., 268:12764–12774 (1993)). Nonetheless, each selectin has a set of preferred biological ligands (Larsen, G. R., Sako, D., Ahern, T. J., Shaffer, M., Erban, J., Sajer, S. A., Gibson, R. M., Wagner, D. D., Furie, B. C., and Furie, B., J. Biol. Chem., 267:11104–11110 (1992); Berg, E. L., Magnani, J., Warnock, R. A., Robinson, M. K., and Butcher, E. C., Biochem. Biophys. Res. Commun., 184:1048–1055 (1992)), although information is lacking on what distinguishes the ligands of one selectin from those of another.

Presently, the best characterized ligands are the HEV-associated ligands for L-selectin, known as GlyCAM-1 (previously terms Sgp50) and Sgp90 (Imai, Y., Singer, M. S., Fenhie, C., Lasky, L. A., and Rosen, S. D., J. Cell Biol., 113:1213–1221 (1991)). These endothelial-associated ligands are mucin-like glycoproteins with sulfated, sialylated and fucosylated O-linked oligosaccharide chains. The glycoproteins were originally detected by precipitation of lymph node extracts, metabolically labeled with $^{35}SO_4$, with a soluble L-selectin/immunoglobulin chimera. Other lower affinity ligands may exist that fail to be precipitated by the chimera but nonetheless participate in functionally significant interactions in the context of cell-cell binding events (Berg, E. L., Robinson, M. K., Warnock, R. A., and Butcher, E. C., J. Cell Biol., 114:343–349 (1991)). GlyCAM-1 is released into conditioned medium of cultured lymph nodes as an intact molecule (Lasky, L. A., Singer, M. S., Dowbenko, D., Imai, Y., Henzel, W. J., Grimley, C., Fennie, C., Gillerr, N., Watson, S. R., and Rosen, S. D., Cell, 69:927–938 (1992); Brustein, M., Kraal, G., Mebius, R. E., and Watson, S. R., J. Exp. Med., 176:1415–1419 (1992)), suggesting that it is a secreted product and/or a loosely associated peripheral membrane component. In contrast, Sgp90 is an integral membrane protein, requiring detergent for extraction (S. Hemmerich and S. Rosen, unpublished results). Molecular analysis has revealed GlyCAM-1 to be a novel mucin-like glycoprotein, and more recently Sgp90 has also been shown to be an HEV-specific glycoform of the mucin CD34, Baumhueter, S., Singer, M. S., Henzel, W., Hemmerich, S., Renz, M., Rosen, S. D. and Lasky, L. A., Science, 262:436–438 (1993). The O-linked chains of GlyCAM-1 have been shown to be heterogeneous in both size and charge (Imai, Y., and Rosen, S. D., Glycoconjugate J., 10:34–39 (1993, )). Some of the chains bear multiple charges, the major contribution apparently coming from sulfation rather than sialylation. The interaction of both GlyCAM-1 and Sgp90 with L-selectin depends on their sialylation, confirming earlier findings that sialidase treatment of lymph node HEV impairs lymphocyte attachment and lymphocyte trafficking (Rosen, S. D., Singer, M. S., Yednock, T. A., and Stoolman, L. M., Science, 228:1005–1007 (1985); Rosen, S. D., Chi, S. I., True, D. D., Singer, M. S., and Yednock, T. A., J. Immunol., 142:1895–1902 (1989)). However, exhaustive desialylation does not completely abrogate the ligand activity of GlyCAM-1, suggesting that a sialic acid-independent mode of recognition also exists (Imai, Y., Lasky, L. A., and Rosen, S. D. Glycobiology, 4:373–381). The sialic acid which forms part of the ligand binding site of GlyCAM-1 appears to be in an $\alpha$2→3 linkage, since the linkage-specific sialidase from Newcastle disease virus partially inactivates GlyCAM-1 as a ligand. Furthermore, both in competitive inhibition studies and direct binding studies, sLe$^x$-type oligosaccharides manifest ligand activity for L-selectin whereas the Lewis X-type structures with $\alpha$2→6 linked NeuSAc are inactive (Foxall, C., Watson, S. R., Dowbenko, D., Fenhie, C., Lasky, L. A., Kiso, M., Hasegawa, A., Asa, D., and Brandley, B. K., *J. Cell Biol.*, 117:895–902 (1992)). An essential contribution from fucose is suspected, since sialyllactose (i.e., NeuSAcα2→3Galβ1→4Glc) as compared to sLe$^x$ is relatively inactive as a competitor of L-selectin binding. Moreover, fucose has been shown to be a critical determinant for the neutrophil ligands for P- and E-selectin (Larsen, G. R., Sako, D., Ahern, T. J., Shaffer, M., Erban, J., Sajer, S. A., Gibson, R. M., Wagner, D. D., Furie, B. C., and Furie, B., *J. Biol. Chem.*, 267:11104–11110 (1992)), and in light of the sequence similarity among the lectin domains of the selectins is likely to be important for L-selectin ligands as well.

The earlier studies have largely focused on which oligosaccharide compounds can act as ligands. We determined that attachment of a sulfate moiety to GlyCAM-1 has a significant effect on the ability of the glycoprotein to act as a ligand (Imai et al., *Nature*, 361:555–557 (1993)) and thereby developed the invention upon which copending application Ser. No. 07/943,817, filed Sep. 11, 1992, and incorporated herein by reference, was based (see also Imai, Y. and Rosen, S. D., *Glycoconjugate J.*, 10:34–39 (1993); Imai, Y., Lasky, L. A. and Rosen, S. D., *Nature*, 361:555–557.

Evidence has been presented that sialyl Lewis X-related oligosaccharides, i.e.,

Siaα2-3Galβ1-4[Fucα1-3]GlcNAc have ligand activity, albeit very weak, for L-selectin (Foxall et al., *J. Cell Biol.*, 117:895–902 (1992), Berg et al., *Biochem. Biophys. Res. Comm.*, 184:1048–1055 (1992), and Imai et al., *Glycobiology*). Based on studies with a carbohydrate-directed antibody, evidence also exists that endogenous HEV-ligands actually possess sialyl Lewis X-related structures (Sawada, M., *Biochem. Biophys. Res. Comm.*, 193:337–347 (1993)). Various sulfated carbohydrates including sulfatide, fucoidin (Imai et al., *J. Cell Biol.*, 111:1225–1232 (1990), related glycolipids (Suzuki et al., *Biochem. Biophys. Res. Comm.*, 190:426–434 (1993) and a sulfated from of Lewis X/a (Green et al., *Biochem. Biophys. Res. Comm.*, 188:244–251 (1992), i.e.,

SO4-3Galβ1-4/3[Fucα1-3/4]GlcNAc have all been shown to have ligand activity for L-selectin. The activity of these carbohydrates depends on their sulfation.

With the information reviewed above, along with further information we developed in our applications discussed below, we began to recognize the importance of sulfation, and began to contemplate methods of affecting sulfation.

Others have isolated and identified a glycosulfatase that removes the sulfate moiety from mucous glycoprotein (see Robertson et al., *Biochem J.*, 293:683–689 (1993)). Further, others have isolated and specifically identified human glucosamine-6-sulfatase and obtained cDNA coding for such (see Robertson et al., *Biochem. Biophys. Res. Commun.*, 157:218–224 (1988)). Finally, others have been able to isolate and specifically identify N-acetylgalactosamine-6-sulfate/galactose-6-sulfate sulfatase (see Tomatsu et al., *Biochem. Biophys. Res. Commun.*, 181:677–683 (1991)).

Our earlier applications Ser. No. 07/943,817 filed Sep. 11, 1992 and Ser. No. 08/155,947 filed Nov. 19, 1993 provide further elaboration on the details of sulfated carbohydrate structures which are ligands for selectins in general and L-selectin in particular. The present invention capitalizes on the specific information developed in our earlier work in order to provide a specific method of treating and/or alleviating inflammation.

SUMMARY OF THE INVENTION

Compositions are administered to a patient (preferably by injection and locally) to treat a variety of conditions including inflammation associated with trauma and with certain aspects of diseases such as rheumatoid arthritis, psoriasis, insulin-dependent diabetes, cutaneous lymphomas, duodenal ulcer, chronic proctitis, lymphocytic thyroiditis, hemorphagic shock, reperfusion injury during transplantation and multiple sclerosis. The compositions are pharmaceutically acceptable injectable formulations which include an active component in a pharmaceutically acceptable carrier. The active component is a chlorate or a selenate which inhibits the natural biochemical sulfation process and/or a sulfatase enzyme which removes a sulfate from a specific position of a saccharide molecule which makes up a part of a natural ligand. Removal of the sulfate from the ligand hinders the ability of the ligand to bind to its natural receptor and thereby hinders a biochemical chain of events which results in inflammation.

An object of the invention is to provide a pharmaceutical formulation comprised of a pharmaceutically acceptable carrier having therein a sulfatase enzyme which removes a sulfate moiety from the 6-position of a saccharide moiety (galactose or N-acetylglucosamine) which makes up a part of a natural ligand.

Another object is to provide such a formulation wherein the sulfatase enzyme is galactose-6-sulfate sulfatase or N-acetylglucosamine 6-sulfate sulfatase.

Another object is to provide a pharmaceutical formulation comprised of a pharmaceutically acceptable carrier having therein a chlorate or a selenate compound, which compound inhibits the natural biochemical sulfation process.

Another object is to provide a method of treating inflammation wherein a formulation comprised of a pharmaceutically acceptable carrier having a chlorate/selenate and/or a specific sulfatase enzyme therein is locally injected to a site or injected intravenously in order to prevent and/or alleviate inflammation.

A feature of the invention is that the sulfatase enzymes used are highly specific for the removal of sulfate moieties from a specific position on a specific ligand for L-selectin, i.e. removal of a sulfate moiety from the 6-position of N-acetylglucosamine and/or the 6-position of galactose.

An advantage of the invention is that a combined effect on reducing inflammation can be obtained by administering combinations of (1) a compound which metabolically inhibits the addition of a sulfate moiety to a natural selectin ligand, and (2) an enzyme which specifically removes a sulfate moiety from a natural ligand.

An important aspect of the invention is pharmaceutical compositions which are useful in treating, preventing and/or alleviating any undesirable effects resulting from the interaction of circulating neutrophils, lymphocytes, monocytes, eosinophils, and basophils with endothelial cells. Such compositions are comprised of an inactive ingredient in the form of a pharmaceutically acceptable excipient material having therein a chlorate and/or a sulfatase enzyme for removing a sulfate from a specific position on an oligosaccharide.

These and other objects, advantages and features of the present invention will become apparent to those persons skilled in the art upon reading the details of the structure, formulation and usage as more fully set forth below, references being made to the accompanying figures and general structural formulae forming a part hereof wherein like symbols refer to like molecular moieties throughout.

BRIEF DESCRIPTION OF THE DRAWINGS

This invention may be better understood and its numerous objects, advantages and features will become apparent to those skilled in the art by reference to the accompanying drawings as follows.

MODES OF CARRYING OUT THE INVENTION

Figure 1:
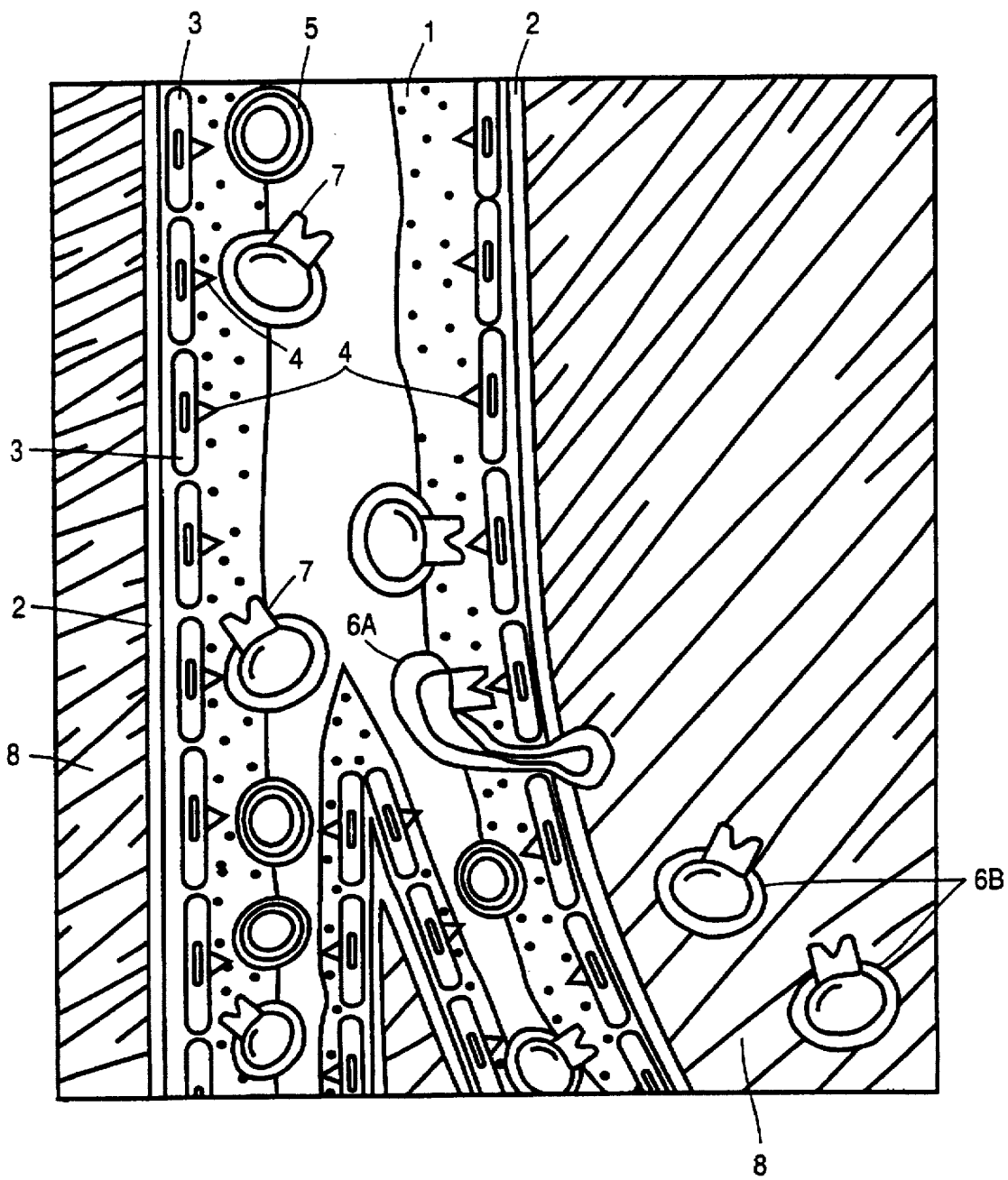
FIG. 1 is a cross-sectional schematic view showing the interaction between white blood cells and activated endothelial cells.

Before the present chlorates and sulfatase enzyme containing compositions and methods of using such are described, it is to be understood that this invention is not limited to the particular compositions, methods or processes described as such compositions and methods may, of course, vary. It is also to be understood that the terminology used herein is for the purpose of describing particular embodiments only, and is not intended to be limiting since the scope of the present invention will be limited only by the appended claims.

As used in this specification and the appended claims, the singular forms "a", "an" and "the" include plural referents unless the context clearly dictates otherwise. Thus, for example, reference to "a sulfated ligand" includes mixtures of such ligands, reference to "the formulation" or "the method" includes one or more formulations, methods and/or steps of the type described herein and/or which will become apparent to those persons skilled in the art upon reading this disclosure and so forth.

All publications cited herein are incorporated herein by reference to disclosure and describe the subject matter for which they are cited in connection with.

Some standard abbreviations used in connection with the present invention include: BSA, bovine serum albumin; DEAE, diethylaminoethyl; DMSO, dimethylsulfoxide; ELAM-1, endothelial/leukocyte adhesion molecule-1 (also E-selectin); HPTLC, high performance thin layer chromatography; LECAM-1, leukocyte/endothelial cell adhesion molecule-1 (also L-selectin); MOPS, 3-[N-Morpholino] propanesulfonic acid; NANA, N-acetylneuraminic acid; PVC, polyvinylchloride; TLC, thin layer chromatography; TFA, trifluoroacetic acid; Tris, tris (hydroxymethyl) aminomethane; C-type, calcium-type; Fuc, fucose; Gal, galactose; GlcN, glucosamine; GalN, galactosamine; GlcNAc, N-acetylglucosamine; GalNAc, N-acetylgalactosamine; Gal-6S, galactose-6-sulfate; GlcNAc-6S, N-acetylglucosamine-6-sulfate; GlcU-S, glucuronic acid-monosulfate; HEV, high endothelial venule; HPAEC, high pH anion exchange chromatography; LacNAc or N-acetyllactosamine, Galβ1→4GlcNAc, Man, mannose; Neu5Ac, N-acetylneuraminic acid; sialyl Lewis X or sLe$^x$, Neu5Acα2→3Galβ1→4(Fucα1→3)GlcNAc; Lewis X or Le$^x$, Galβ1→4(Fucα1→3)GlcNAc; Lewis a or Le$^a$, Galβ1→3(Fucα1→4)GlcNAc; SGNL, 3-sulfoglucuronylneolacto glycolipids; SDS-PAGE, sodium dodecylsulfate polyacrylamide gel electrophoresis, Sgp50, sulfated glycoprotein of 50 kDa; Sgp90, sulfated glycoprotein of 90 kDa.

General Overview

The ability of leukocytes in the blood to bind to endothelial cells which line blood vessels is known. Substantial work has been done on isolating and characterizing ligands which bind to selectin receptors thereby making the leukocyte cell to endothelial cell binding possible. Our earlier work demonstrated that natural ligands for L-selectin include sulfate moieties. We also found that the sulfates were generally present at a specific position on the oligosaccharide molecule which comprises the ligand and that removal of the sulfate drastically impaired the ability of the ligand to bind to a selectin receptor. Impairing such binding interrupts the biochemical chain of events which, in excess, leads to inflammation. By interrelating such facts we deduced that it would be possible to alleviate and/or prevent inflammation in two ways. First, we endeavored to find a compound which would inhibit sulfation, i.e. inhibit the addition of a sulfate moiety onto a natural selectin ligand—thereby preventing complete formation of the ligand. We found that chlorates act to inhibit biochemical sulfation o GlyCAM-1 and CD34/ Sgp90 and thereby prevent their ability to bind to L-selectin. Second, we endeavored to identify the exact sulfate substitutions on the carbohydrates of a natural ligand for L-selectin (i.e. GlyCAM-1). We showed that galactose-6 sulfate and N-acetylglucosamine-6-sulfate are equally present in GlyCAM-1. Thus, specific sulfatases which remove these sulfate modifications from the ligands of L-selectin will inactivate the ligands and significantly impair binding to L-selectin. Before describing the sulfation inhibitors such as chlorate compounds and sulfatase enzymes used in connection with the present invention a description of how ligands operate in vivo is provided.

In vivo Function of Ligands

FIG. 1 shows a cross-sectional view of a blood vessel 1. The vessel wall 2 is lined internally with endothelial cells 3. The white blood cells 6 synthesize and express L-selectin which is displayed in FIG. 2 as a surface receptor 7. Both red blood cells 5 and white blood cells 6 flow in the vessel 1. The white blood cells 6 display a receptor 7 which have chemical and physical characteristics which allow the receptor 7 to bind to the ligand 4 on the endothelial cells 3. Once the receptor 7 binds to the ligand 4, the white blood cell 6 is brought through the vessel wall 2 as is shown with the white blood cell 6A. The white blood cells 6B brought into the surrounding tissue 8 can have positive effects, such as fighting infection, and negative effects, such as inflammation. Inflammation is caused by too many white blood cells 6B entering the tissue 8 in a given unit of time.

We found that natural ligands 4 includes sulfates on specific positions and that (1) it is possible to inhibit the sulfation of the natural ligand by introducing a competing moiety such as a chlorate which inhibits sulfation and (2) a sulfate can be removed from a specific position by a specific sulfatase enzyme thereby rendering the binding of the natural ligand and receptor.

Figure 2:
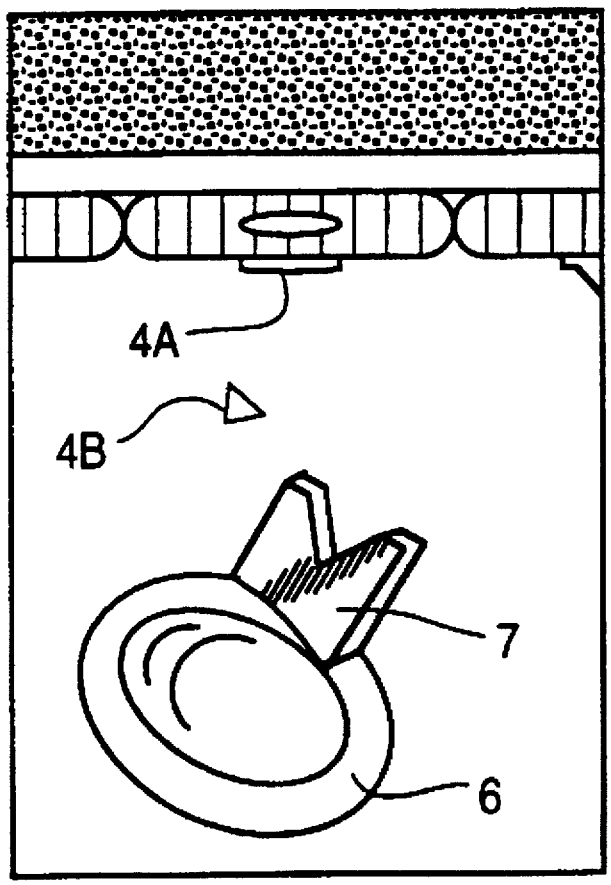
FIG. 2 is a cross-sectional schematic view showing how sulfatase enzymes of the invention might be used to remove a sulfate moiety from a natural ligand.

FIG. 2 shows how removal of the sulfate 4B hinders the ability of the unsulfated ligand 4A to bind to the receptor 7. Thus, FIG. 2 shows how compounds which inhibit sulfation or remove a sulfate can, when administered, inhibit the adhesion of a receptor 7 (connected to a white blood cell 6) to a natural ligand 4 on an endothelial cell 3. By administering pharmaceutically effective amounts of chlorates/ selenates to inhibit sulfation and/or sulfatase enzymes to remove sulfate moieties at specified positions, some, but not all, of the white blood cells will not reach the surrounding tissue 8. By slowing the rate at which the white blood cells reach the surrounding tissue, inflammation can be prevented and/or alleviated.

In accordance with the above description and the schematic diagrams of FIGS. 1 and 2, it can be seen that by including a compound which prevents sulfation of the endothelial ligand, the ligand 4 would not be sulfated and therefore would have a configuration such as the ligand 4A. Such a configuration would not adhere well (although it can adhere) to the receptor 7 thereby reducing the rate at which leukocytes adhere to endothelial cells and enter the tissue 8, thus preventing or alleviating inflammation. In that any inhibitor would not block all sulfation the inhibitor could be used with a sulfatase in order to remove sulfates to create an unsulfated ligand 4A and cause the same effect, i.e. hinder ligand/receptor binding. Thus, by combining inhibitors such as chlorates or sodium selenate with sulfatases, a combined effect can be obtained with respect to preventing the adhesion between the white blood cells and the endothelial cells which combined effect can prevent and/or alleviate inflammation.

The Importance of Sulfation

Prior to the discovery that HEV ligands are, in fact, sulfated, we suspected the potential importance of sulfation for their function based on the potent ligand activity of a number of other sulfated carbohydrates (e.g., fucoidin, sea urchin egg jelly fucan, and sulfatide) for L-selectin (Stoolman, L. M., and Rosen, S. D., *J. Cell Biol.*, 96:722-729 (1983); Stoolman, L. M., Yednock, T. A., and Rosen, S. D., *Blood*, 70:1842-1850 (1987); Imai, Y., True, D. D., Singer, M. S., and Rosen, S. D., *J. Cell Biol.*, 111:1225-1232 (1990); True, D. D., Singer, M. S., Lasky, L. A., and Rosen, S. D., *J. Cell Biol.*, 111:2757-2764 (1990)). Thereafter, although the importance of sulfation was not known, it was demonstrated that 3-sulfated $Le^x/Le^a$ (i.e., sulfated on 3-position of galactose), SGNL, and other sulfated structures are also capable of binding to L-selectin, apparently through specific interactions with its C-type lectin domain (Green, P. J., Tamatani, T., Watanabe, T., Miyasaka, M., Hasegawa, A., Kiso, M., Yuen, C. T., Stoll, M. S., and Feizi, T., *Biochem. Biophys. Res. Commun.*, 188:244-251 (1992); Suzuki, Y., Toda, Y., Tamatani, T., Watanabe, T., Suzuki, T., Nakao, T., Murase, K., Kiso, M., Hasegawa, A., Tadano-Aritomi, K., Ishizuka, I., and Miyasaka, M., *Biochem. Biophys. Res. Commun.*, 190:426-434 (1993); Needham, L. K., and Schnaar, R. L., *Proc. Natl. Acad. Sci. USA*, 90:1359-1363 (1993)).

The essential role of sulfation in the activity of these various carbohydrates caused us to focus our attention on the contribution of sulfation to GlyCAM-1 ligand activity. We have demonstrated (using chlorate as a metabolic inhibitor of sulfation) that sulfation of GlyCAM-1 (independent of its overall sialylation and fucosylation) plays an essential role in ligand activity for L-selectin (Imai, Y., Lasky, L. A., and Rosen, S. D., *Nature*, 361:555-557 (1993)). The importance of sulfation also holds for Sgp90/CD34. There are other examples of biologically significant recognition determinants that are defined by sulfate modifications of carbohydrates (Glabe, C. G., Grabel, L. B., Vacquier, V. D., and Rosen, S. D., *J. Cell Biol.*, 94:123-128 (1982); Kjellen, L., and Lindahl, U., *Ann. Rev. Biochem.*, 60:443-475 (1991); Rapraeger, A. C., Krufka, A., and Olwin, B. B., *Science*, 252:1705-1708 (1991); Roche, P., Debellé, F., Maillet, F., Lerouge, P., Faucher, C., Truchet, G., Dénarié, J., and Promém J. C., *Cell*, 67:1131-1143 (1991); Fiete, D., Srivastava, V., Hindsgaul, O., and Baenziger, J. U., *Cell*, 67:1103-1110 (1991); Cerami, C., Frevert, U., Sinnis, P., Takacs, B., Clavijo, P., Santos, M. J., and Nussenzweig, V., *Cell*, 70:1021-1033 (1992); Pancake, S. J., Holt, G. D., Mellouk, S., and Hoffman, S. L., *J. Cell Biol.*, 117:1351-1357 (1992); Guo, N. H., Krutzsch, H. C., Negre, E., Vogel, T., Blake, D. A., and Roberts, D. D., *Proc. Natl. Acad. Sci. USA*, 89:3040-3044 (1992); Needham, L. K., and Schnaar, R. L., *J. Cell Biol.*, 121:397-408 (1993)). These publications support the basic theory behind the present invention.

Inhibitor of Sulfation

Chlorate is a metabolic inhibitor of carbohydrate sulfation (Baeuerle and Huttner, *Biochem Biophys. Res. Comm.*, 141:870 (1986)). Accordingly, chlorate was used to test whether sulfation is required for the ligand binding activity of GlyCAM. When tests were carried out it was found that the presence of chlorate (10 mM) in organ cultures of lymph nodes substantially reduced (≈90%) incorporation of $^{35}$S-SO$_4$ into GlyCAM and CD34 and completely eliminated binding to L-selectin. Binding of GlyCAM to a sialic acid specific lectin (Limax agglutinin) or to a fucose-specific lectin (Aleuria aurantia agglutinin) was unchanged, indicating that sialylation and fucosylation of the molecule were not altered by the presence of chlorate.

By measuring incorporation of [$^3$H]-fucose into GlyCAM directly, it was confirmed directly that the level of fucosylation was not affected by chlorate. It was also demonstrated that chlorate did not affect the rate of synthesis of the protein core of GlyCAM or CD34. Taken together, these results establish that sulfate is very important for the interaction of GlyCAM and CD34 with L-selectin. In that sialyl-Lewis X (i.e., $sLe^x$) possesses ligand activity for L-selectin we have been able to deduce that the key carbohydrate chains of GlyCAM involve a sulfate-modification of a $sLe^x$-like oligosaccharide.

Inhibitor of sulfation include sodium chlorate (Baenerle et al., *Proc. Natl. Acad. Sci. USA*, 141:2:870-877 (1986)) and sodium selenate (Hilz & Lipmann, *Proc. Natl. Acad. Sci. USA*, 880-890 (1955)). Both of these inhibitors work by blocking the formation of 3' phosphoadenosine 5' phosphosulfate (PAPS), which is essential for the biosynthesis of sulfated molecules.

Endothelial ligands for L-selectin are available in very limited quantities. Desulfation reduces the affinity of these ligands for L-selectin such that leukocyte adhesion is blocked.

Inhibiting the Metabolic Sulfation of L-selectins

Slices of mouse lymph nodes were cultured with $^{35}$S-sulfate in the presence and absence of 10 mM sodium chlorate. Detergent lysates were prepared and subjected to precipitation with several reagents that recognize GlyCAM-1. With a peptide antibody that binds to the polypeptide core of GlyCAM-1, the amount of labeled GlyCAM immunoprecipitated from the chlorate-treated culture was substantially reduced compared to that of the control culture. As determined by direct scintillation counting, chlorate treatment reduced the radioactivity immunoprecipitated by the peptide antibody to 12% of the control level. Culture in chlorate resulted in a similar reduction in the amount of $^{35}$S-sulfate precipitated by Limax agglutinin (11.4% of control) and Aleuria aurentia lectin (13.7% of control), lectins that react with sialic acid and fucose, respectively. SDS-PAGE analysis demonstrated that this reduction was reflected in the commensurately reduced autoradiographic intensity of GlyCAM-1. In contrast to these findings, LEC-IgG, the immunoglobulin chimera of L-selectin Watson, S. R., Imai, Y., Fennie, C., Geoffroy, J. S., Rosen, S. D. & Lasky, L. A., *J. Cell Biol.*, 110:2221-2229 (1990) failed to precipitate a detectable GlyCAM-1 band from the chlorate-treated culture, whereas a strong band was seen in the control. Only a background level (0.9% of control) of radioactivity was measured in the precipitate from the chlorate-treated culture.

These findings indicate that chlorate, as a consequence of its general inhibition of sulfation, reduced sulfate incorporation into GlyCAM-1 to about 10–15% of the control, as inferred from the ratio of counts precipitated by the peptide antibody. There was no apparent effect of chlorate on the overall sialylation or fucosylation of the molecule, since the reduction in Aleuria and Limax precipitated $^{35}$S-SO$_4$ counts closely paralleled the reduction in sulfate incorporation. However, the binding of LEC-IgG to GlyCAM, which represents the functional interaction of interest, was completely abrogated by culture in chlorate.

Inhibitors such as chlorates, including sodium and potassium chlorates, and inhibitors such as selenate act as metabolic inhibitors of sulfation by preventing the formation of PAPS, which is the general donor of sulfates in the biosynthesis of sulfated biological molecules. Accordingly, the use of such inhibitors can have other, undesirable effects, in that they can prevent the sulfation of molecules which should be sulfated. Accordingly, it would be desirable to provide a sulfation inhibitor which prevents the sulfation only of L-selectin ligands, such as by using an inhibitor which inhibits sulfation of a specific carbohydrate chain of such glycoproteins. Specifically, the inhibitor should inhibit by preventing the addition of a sulfate to the 6-position of galactose (or the 6-position of N-acetylglucosamine) which are present in the endothelial ligands of L-selectins.

Other Effects of Chlorate on L-selectin

To determine directly whether the fucosylation of GlyCAM-1 was affected by chlorate, $^3$H-fucose was employed as a metabolic precursor. The peptide antibody precipitated approximately the same number of cpm from detergent lysates obtained from the chlorate and control cultures; moreover, the autoradiographic intensity of the GlyCAM-1 component was comparable in both conditions. However, while LEC-IgG precipitated GlyCAM-1 in the control culture, LEC-IgG precipitated only a background level of counts (7% of control) from the chlorate-treated culture and there was no detectable GlyCAM-1.

To determine what effect chlorate had on the synthesis of the protein core of GlyCAM-1, we employed $^3$H-threonine as a metabolic label. When conditioned medium was analyzed, LEC-IgG precipitated a prominent GlyCAM-1 component from the control culture but did not react with any components when chlorate was present during the culture. With or without chlorate treatment, two antibodies against the core protein of GlyCAM-1 precipitated broad bands that ran at ≈50K.

Taken together, these results indicate that chlorate substantially inhibits the sulfation of GlyCAM-1 but allows biosynthesis of the protein core as well as sialylation and fucosylation of its carbohydrate chains to proceed normally. The complete loss of reactivity with LEC-IgG establishes the importance of sulfation for binding. As the O-linked carbohydrate chains of GlyCAM-1 have been shown to be sulfated and the polypeptide has only one potential tyrosine residue for sulfate addition, we concluded that the critical sulfates must be on the carbohydrate chains. CD34/Sgp90 is also a sulfated ligand of L-selectin. When the sulfation of this molecule was inhibited by chlorate treatment its ability to interact with L-selectin was also drastically inhibited.

Determination of the Sulfated Oliogosaccharides of GlyCAM-1

As reviewed above, the sulfation of GlyCAM-1 and CD34/Sgp90 (two endothelial-associated ligands) are required for their interaction with L-selectin. In that sulfatases are specific (i.e., remove sulfation from a specific position) it was essential to define the exact sulfation modifications of the carbohydrates of these natural ligands. GlyCAM-1 was metabolically labeled in lymph node organ culture with $^{35}$SO$_4$ and a panel of tritiated carbohydrate precursors. Mild hydrolysis conditions were established that released sulfated oliogosaccharides without cleavage of sulfate esters. Low molecular weight and singly charged fragments, obtained by a combination of gel filtration and anion exchange chromatography, were analyzed. The structural identification of the fragments relied on the use of a variety of radiolabeled sugar precursors, further chemical and enzymatic hydrolysis, and high pH anion exchange chromatography analysis. Sulfated constituents of GlyCAM-1 were identified as Gal-6-SO$_4$, GlcNAc-6-SO$_4$, (SO$_4$-6)Galβ1→4GlcNAc and Galβ1→4(SO$_4$-6)GlcNAc.

Sialic acid and fucose are also essential for the activity of GlyCAM-1 and CD34/Sgp90 (Imai, Y., Lasky, L. A., and Rosen, S. D. Glycobiology, 2:373–381 (1992)). In order to define the relationship of sialic acid and fucose to the sulfated mono- and disaccharides of GlyCAM-1, we employed lectins of defined specificity in conjunction with specific exo-glycosidases to identify a major capping structure that includes all three critical elements. The complementary reactivity of Maackia amurensis agglutinin (Knibbs, R. N., Goldstein, I. J., Ratcliffe, R. M., and Shibuya N. (1991), J. Biol. Chem., 266:83–88 (1991), with fully sialylated, undersulfated GlyCAM-1 and of Sambucus nigra agglutinin/Trichosanthes japonica agglutinin (Yamashita, K., Umetsu, K., Suzuki, T., and Ohkura, T., Biochemistry, 31:11647–50 (1992) with desialylated, but normally sulfated GlyCAM-1 indicates the presence of terminal 6'-sulfated sialyllactosamine, i.e.,

Siaα2→3(SO$_4$-6)Galβ1→4GlcNAc.

To identify the substitution of fucose, we took advantage of Streptomyces α(1→3/4) fucosidase (Maemura, K., and Fukuda, M., J. Biol. Chem, 267:24379–24386 (1992). This enzyme removes fucose almost quantitatively from asialo-GlyCAM-1 while substantially enhancing its binding to Lycopersican esculentum agglutinin, a lectin with specificity for β1→4 linked GlcNAc (Merkle, R. K. and Cummings, R. D., J. Biol. Chem., 262:8179–8189 (1987). These results indicate the presence of Fuc in an α1→3 linkage to GlcNAc. The finding of a strict requirement for desialylation to achieve defucosylation of GlyCAM-1 indicates a proximal location of Fuc with respect to terminal sialic acid. The nature of the capping group was further defined by studying the effects of sulfation, sialylation, and fucosylation on the ability of exo-β(1→4) galactosidase (Maemure, K., and Fukuda, M., J. Biol. Chem., 267:24379–24386 (1992) to release [$^3$H-Gal] from GlyCAM-1. These results, in concert with the hydrolysis analysis above, indicate that 6'-sulfated, sialyl Lewis x, i.e.,

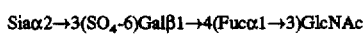

Siaα2→3(SO$_4$-6)Galβ1→4(Fucα1→3)GlcNAc is a major capping group of GlyCAM-1. This structure is a modification of sialyl Lewis x, which has been shown to have weak ligand activity for L-selectin (Imai, Y., Lasky, L. A., and Rosen, S. D., Glycobiology, 2:373–381 (1992). It is not known at present whether the GlcNAc in the capping structure above is modified by 6 sulfation or whether α(1→3) fucosylation and 6-sulfation represent mutually exclusive substitutions on the GlcNAc residues. A list of possible structures are specified in our application, Ser. No. 08/155,947 filed on Nov. 19, 1993.

Thus, we have determined that the following two structures represent the major sulfation modifications of monosaccharides within GlyCAM-1:

and

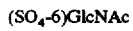

Since sulfation is essential for the ligand activity of GlyCAM-1, the use of specific sulfatases to remove these sulfates in vivo will be useful in greatly reducing leukocyte entry into inflammatory sites.

Sulfatase Enzymes

Sulfatase enzymes are known. Further, it is known that sulfatase enzymes can be extracted from natural sources or recombinantly produced. The sulfatase enzymes used in connection with the formulations and methodology of the present invention can be extracted from natural sources and purified or recombinantly produced. In general, extraction and/or recombinant production of the sulfatase enzyme takes place followed by purification using methodology known to those skilled in the art. The sulfatase enzymes may be extracted from sources such as bacteria, fungi, plants, invertebrates, mammalian sources such as liver, kidney, placenta, brain, leukocytes, or endothelial cells. Although extraction and purification is possible, it is somewhat cumbersome. Accordingly, it is preferable to obtain the sulfatase enzymes of the present invention using recombinant technologies.

Sulfatase enzymes act very specifically. Any given sulfatase enzyme is generally useful only with respect to removing a sulfate moiety from a specific position on a specific molecule. In that we have determined that sulfate moieties are present at specific positions on specific saccharide molecules of ligands (see below), it is necessary to obtain the specific sulfatase enzyme which removes the sulfate moiety in order to carry out the present invention. The functionality of either an extracted or a recombinantly produced enzyme can be readily confirmed by those skilled in the art. This is done by placing the enzyme in contact with a sulfated selectin ligand under appropriate conditions, and thereafter determining the degree of removal of sulfate moieties from the ligand. Pursuant to the present disclosure, the removal of the sulfate moiety can be confirmed by noting the removal as it relates to the fact that the ligand is substantially hindered with respect to its ability to bind to a selectin receptor.

Specific sulfatase enzymes pertinent to the sulfation modifications of GlyCAM and CD34/Sgp90 are disclosed in Robertson et al., *Biochem. J.*, 293:683-689 (1993), Robertson et al., *Biochem. Biophys. Res. Commun.*, 157:218-224 (1988), and Tomatsu et al., *Biochem. Biophys. Res. Commun.*, 181:677-683 (1991). Each of these publications is incorporated herein by reference in order to disclose and describe sulfatase enzymes, the amino acid sequences of those enzymes, the DNA sequences which encode the sulfatase enzymes, and methods of recombinantly producing the enzymes and thereafter purifying same.

Preferred sulfatase enzymes useful in connection with the present invention include N-acetyl-galactosamine-6-sulfate/galactose-6 sulfate sulfatase, N-acetylglucosamine-6-sulfate sulfatase. In that we have found that sulfate moieties are present at the 6-position of galactose and N-acetylglucosamine molecules of selectin ligands, the sulfatases which are useful in connection with the present invention are preferably capable of removing these sulfate moieties.

Use and Administration

The compounds such as (1) various chlorates, (2) sulfatases, and (3) combinations thereof can be formulated into a pharmaceutical formulation and administered to a subject in need thereof to treat a patient. They may be administered prophylactically in order to prevent inflammation or to relieve it after it has begun. The sulfatases as well as metabolic inhibitors of sulfation such as sodium or potassium chlorate and sodium selenate are preferably administered with a pharmaceutically acceptable carrier, the nature of the carrier differing with the mode of administration, for example, oral administration, usually using a solid carrier and I.V. administration a liquid salt solution carrier. The formulation and/or means of administration will also vary depending on whether a chlorate or sulfatase is being administered. A sulfatase is an enzyme which would not generally be administered orally but would be administered by I.V.

The desired formulation can be made using a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of chlorates or selenates directly in transdermal formulations with permeation enhancers such as DMSO. Other topical formulations can be administered to treat dermal inflammation.

A therapeutically effective amount is an amount sufficient to prevent sulfation or remove sulfate moieties from a substantial proportional number of ligands so that inflammation can either be prevented or ameliorated. Thus, "treating" as used herein shall mean preventing or ameliorating inflammation and/or symptoms associated with inflammation. Typically, the compositions of the instant invention will contain from less than 1% to about 95% of the active ingredient, preferably about 10% to about 50%. Preferably, between about 100 mg and 500 mg will be administered to a child and between about 500 mg and 5 grams will be administered to an adult. Administration is preferable by injection and more preferable injection to a localized area. The frequency of administration will be determined by the care given based on patient responsiveness. Other effective dosages can be readily determined by one of ordinary skill in the art through routine trials establishing dose response curves.

In order to calculate the amount of sulfatase enzyme, those skilled in the art could use readily available information with respect to the amount of enzyme necessary to remove a given amount of sulfatase. For example, if a given enzyme has an activity such that one unit of the enzyme removes 1 micromole/min. of $SO_4$ from L-selectin ligands at physiological pH, then one would administer from 1 to 10 units intravenously to a 70 kg. human for therapeutic purposes. The amount of chlorate or other inhibitor necessary to inhibit the sulfation can also be calculated from in vitro experimentation. For example, by calculating the amount of chlorate necessary to inhibit sulfation of a given amount of L-selectin ligands and estimating the amount of such ligands within the area to be treated, an amount of chlorate to be administered can be determined. The amount of inhibitor will, of course, vary depending upon the particular inhibitor used.

In determining the dose of sulfatases or chlorates (or selenates) to be administered, it must be kept in mind that one does not wish to completely inhibit sulfation or remove all sulfates. In order for a normal healing process to proceed, at least some of the white blood cells or neutrophils must be brought into the tissue in the areas where the wound, infection or disease state is occurring. The amount of the sulfatases or chlorates/selenates administered are adjusted based on the particular needs of the patient while taking into consideration a variety of factors such as the type of disease that is being treated.

It is believed that the sulfatases and/or chlorates/selenates can be used to treat a wide range of diseases, including diseases such as rheumatoid arthritis, asthma, adult respiratory distress syndrome, sarcoidosis, hypersensitivity pneumonitis multiple sclerosis and the spread of lymphomas to cutaneous sites. The compositions of the invention should be applicable to treat any disease state wherein the immune system turns against the body causing the white cells to accumulate in the tissues to the extent that they cause tissue damage, swelling, inflammation and/or pain. The inflammation of rheumatoid arthritis, for example, is created when large numbers of white blood cells quickly enter the joints in the area of disease and attack the surrounding tissues.

Formulations of sulfatases and/or chlorates/selenates of might also be administered to prevent the undesirable after-effects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The white blood cells possess L-selectin. The receptors adhere to ligand molecules on the surface of activated endothelial cells. The ligand molecules may be induced to the surface of the endothelial cells by activation. Large numbers of white blood cells are quickly captured and brought into the tissue surrounding the affected area, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. This is most preferably done by local injection of sulfatases and/or chlorates/selenates to the area subjected to trauma. Also, patients suffering from hemorphagic shock could be treated to alleviate inflammation associated with restoring blood flow. Other disease states which might be treatable using formulations of the invention include various types of arthritis, various chronic inflammatory conditions of the skin, insulin-dependent diabetes, and adult respiratory distress syndrome. After reading the present disclosure, those skilled in the art will recognize other disease states and/or symptoms which might be treated and/or mimitigated by the administration of formulations of the present invention.

Other modes of administration will also find use with the subject invention. For instance, sulfatases and/or chlorates/selenates of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

A variety of different respiratory diseases exhibit symptoms which are aggravated by inflammation and all aspects of the present invention can be used in the treatment of such diseases in order to alleviate and/or prevent the aggravation of such symptoms. This is preferably done by the topical pulmonary administration of the sulfatases and/or chlorates/selenates of the invention. Such compounds can be topically delivered to the passages of the lung surface. Aerosol formulations may be delivered by the use of conventional metered dose inhalers (MDIs). By formulating any or all of the sulfatases or chlorates/selenates in combination with a suitable propellant and delivering the formulation via an MDI, relief from pulmonary inflammation can be obtained in a very short period of time.

Sulfatases and/or chlorates/selenates of the invention are preferably administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the chlorate/selenate and/or sulfatase adequate to achieve the desired state in the subject being treated.

As indicated above, the primary indication of the sulfatase enzymes and sulfate inhibitors is to prevent or alleviate inflammation. However, L-selectin has been implicated in the spread of lymphomas to cutaneous sites (see Michie, S. A., et al., *American Journal of Pathology*, 143:1688–1698 (1993)). The use of sulfatases and sulfate inhibitors could aid in preventing hematogenous spread of lymphomas or other hematopoietic neoplasms to cutaneous sites. In order for various forms of cancer to spread within a human body, the cancerous cells leave the original tumor and thereafter attach on another site, where the cancerous growth continues. By administering sulfatase enzymes and/or sulfate inhibitors as described herein, the reattachment of the cancerous cell to another site would be hindered or prevented.

The various sulfatases and chlorates/selenates of the present invention can be used by themselves, with each other, or in combination with pharmaceutically acceptable excipient materials as described above.

EXAMPLES

The following examples are put forth so as to provide those of ordinary skill in the art with a complete disclosure and description of methodologies carried out in order to demonstrate the importance of sulfate groups present on L-selectin ligands with respect to their interaction and/or binding with L-selectin. These examples are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, parts are parts by weight, molecular weight is weight average molecular weight, temperature is in degrees Centigrade, and pressure is at or near atmospheric.

Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, preferred methods and materials are now described. All publications mentioned herein are incorporated herein by reference.

Example 1

Inhibition of GlyCAM-1 sulfation eliminates its interaction and/or binding with L-selectin. This conclusion was reached when lymph nodes were metabolically labelled in organ culture with (a) [$^{35}$-S]-sulfate or (b) [$^{3}$-H]-fucose in the presence or absence of chlorate and detergent lysates were subjected to precipitation with L-selectin chimera (LEC-IgG), a rabbit anti-Sgp50 peptide antibody (anti-peptide 2), rabbit preimmune serum, Limax flavus agglutinin (sialic acid specificity), or Aleuria aurantia agglutinin (AAA; fucose specific). The apparent molecular weight of [$^{3}$-H]-fucose-labelled GlyCAM-1 was slightly larger in the presence of chlorate, probably because the reduced sulfation retards electrophoretic mobility.

Pooled mesenteric and peripheral lymph nodes from ICR mice (80 mg wet weight per condition) were incubated with (a) 250 µCi of [$^{35}$-S]-sodium sulfate (ICN) or (b) 250 µCi of [5,6 $^{3}$-H]-L-fucose (ICN) in the presence or absence of 10 mM Na chlorate (Aldrich) in 0.5 ml of RPMI-1640 with 25 mM HEPES (1/10 sulfate concentration) for 4 h at 37° C. Tissue was extracted with 1.2 ml of 2% Triton X-100 (Boehringer Mannheim) in Dulbecco's PBS containing 1 mM PMSF (Sigma), 1% (v/v) aprotinin (Sigma), 10 µg/ml of pepstatin (Boehringer Mannheim) and 0.02% NaN$_3$ (lysis buffer) as described previously[11]. The lysates were boiled 3 min and the supernatants were precleared with 100 µl of Protein A Sepharose (Zymed) overnight. Aliquots of the precleared supernatants were added to 10 µl beads of LEC-IgG-Protein A Sepharose Beads (30 µg LEC-IgG per 10 µl beads), rabbit anti-peptide 2-Protein A beads (10 µl serum per 10 µl beads), rabbit preimmune serum-Protein A beads (10 µl serum per 10 µl beads), Limax flavus agglutinin-Sepharose beads (20 µg protein per 10 µl beads), or Aleuria aurantia agglutinin-Sepharose beads (10 µg protein per 10 µl beads), and incubated for 4 h at 4° C. on a rocker. The beads were washed in the lysis buffer (6 times), and the 1/14 aliquots of beads were saved for direct counting by a scintillation counting and the remainder of beads were solubilized in Laemmli sample buffer (without beta mercaptoethanol) and run by on a 10% acrylamide gel (nonreducing condition) with fluorography employing ENHANCE (New England Nuclear). Molecular weight markers (BioRad) were phosphorylase B (97.4K), BSA (66.2K), ovalbumin (45K), carbonic anhydrase (31K), soybean trypsin inhibitor (21.5K). LEC-IgG and antiserum were coated on Protein A-Sepharose beads by rocking overnight at 4° C. Lectin beads were prepared by coupling Limax agglutinin (Calbiochem) and AAA (Boehringer Mannheim) to CNBr-activated Sepharose 4B (Sigman). Miller, R., *Meth. Enzymol.* 138:527–536 (1987).

Example 2

Inhibition of GlyCAM-1 sulfation eliminates its interaction and/or binding with L-selectin. This conclusion was reached when aliquots of the same precipitates of Example 1, labeled with (a) [$^{35}$-S]-sulfate or (b) [$^{3}$-H]-fucose in the presence (dark bars) or absence (cross-hatched bars) of chlorate were subjected to scintillation counting. The percents shown in a given panel (a) (not shown) indicate the percent counts obtained in the presence of chlorate as compared to the absence of chlorate. The values for anti-peptide 2, Limax, and AAA were essentially the same, reflecting the overall reduction in sulfation. In an independent experiment, the corresponding values were: 6% (for LEC-IgG), 35.6% (for anti-peptide 2), 35.3% (for Limax).

Example 3

Inhibition of GlyCAM-1 sulfation eliminates its interaction and/or binding with L-selectin. This conclusion was reached when lymph nodes were labeled with L-[3-$^{3}$H]-threonine in the presence or absence of chlorate. Conditioned medium (a) or detergent extracts (b) were subjected to precipitation with LEC-IgG, rabbit anti-Sgp50 anti-peptide antibodies (anti-peptide 1, 2, 3), or rabbit preimmune serum.

Mouse lymph nodes were labeled with 750 µCi of L-[3-$^{3}$H] threonine (Amersham) in 0.5 ml of threonine free-1/10 sulfate concentration-RPMI 1640 containing 25 mM HEPES for 4 h at 37° C. in the absence or the presence of 10 mM sodium chlorate. Detergent lysates were boiled, precleared and subjected to precipitation with the indicated reagent as described in Example 1. Conditioned media were precleared and precipitated in parallel. The bead-bound material was analyzed on SDSPAGE under reducing conditions with fluorography. In the anti-peptide antibody lanes, the =50K component was compressed by the immunoglobulin heavy chain.

Example 4

Metabolic labeling of murine lymph nodes

For metabolic labeling (Imai, Y., Lasky, L. A., and Rosen, S. D., *Nature*, 361:555–557 (1993), axillary, brachial, cervical, and mesenteric lymph nodes were dissected from five ICR mice, diced with a razor-blade, and incubated in 1 ml of RPMI-1640, supplemented with penicillin (100 units/ml) and streptomycin (0.1 mg/ml). The tissue was cultured for 4 h (37° C.) in the presence of D-[6-$^{3}$H]-galactose, D-[6-$^{3}$H]-glucosamine, D-[2$^{3}$-H]-mannose (at 0.5 mCi/ml, all from Du Pont New England Nuclear, Boston, Mass.), L-[5,6-$^{3}$H]-fucose, or Na$_2$$^{35}$SO$_4$ (at 1 mCi/ml, both from ICN, Costa Mesa, Calif.). Labeling with $^{35}$SO$_4$ was carried out in a mixture of 90% sulfate-free RPMI-1640 and 10% standard RPMI-1640. Conditioned medium was collected from the culture and cleared by centrifugation for 5 min at 10,000×g.

Immunoprecipitation of GlyCAM-1

All steps were carried out at 4° C. GlyCAM-1 was immunoprecipitated from the conditioned medium by the addition of 20 µl of protein A-Sepharose 4B (Zymed, So. San Francisco, Calif., 2.5 mg recombinant protein A/ml gel) derivatized with rabbit polyclonal antibody directed to the peptide CKEPSIFREELISKD (pep2) from the deduced GlyCAM-1 protein core (Lasky, L. A., Singer, M. S., Dowbenko, D., Imai, Y., Henzel, W. J., Grimley, C., Fennie, C., Gillerr, N., Watson, S. R., and Rosen, S. D., *Cell*, 69:927–938 (1992)). The matrix was washed five times in Tris-buffered saline (TBS: 10 mM Tris-HCl pH 7.4, 150 mM NaCl) and bound ligand was eluted from the matrix by the addition of 200 μl TBS containing free pep2 (1 mg/ml). One tenth of the preparation (20 μl) was subjected to SDS gel electrophoresis on a 10% polyacrylamide gel according to Laemmli (Laemmli, U. K., *Nature*, 227:680–685 (1970)), followed by fluorography using Enhance (New England Nuclear).

Mild acid hydrolysis of GlyCAM-1

The above ligand preparation was treated with 0.2M $H_2SO_4$ (final volume 250 μl), overlayed with clear mineral oil (Sigma), and incubated at 100° C. for 30 min.

Thin layer chromatography

After neutralization of the hydrolysate with 50 μl of 2N $NH_4OH$, two 1 μl-aliquots were applied to a 100 mm×50 mm silica gel-coated glass plate (60 F254, Merck, Darmstadt, Germany). Two 0.5 μl aliquots of 1 mM $Na^{35}SO_4$ solution (5000 cpm each) were then applied to the same plate, with one aliquot overlayed into the hydrolyzed material and the second in a separate lane. The plate was developed in n-BuOH/N,N-dimethylformamide (DMF)/1M sodium borate pH 9, 50:20:25, followed by fluorography with Enhance spray (New England Nuclear).

Initial fractionation of mild acid hydrolysate by gel filtration

The neutralized hydrolysate was combined with 50 μl of 2.5% hemoglobin (Sigma) in 0.1M pyridine-acetate pH 5.4 and loaded onto a column of Biogel P4 (200–400 mesh, Bio-Rad Laboratories, Richmond, Calif., 112 cm×1 cm, bed volume=88 ml) in pyridine-acetate (0.1M, pH 5.4). The column was eluted at 22° C. with the same pyridine-acetate buffer at a rate of 5 ml/h, and 30-drop fractions (0.83–0.87 ml) were collected. A 40 μl sample of each fraction was mixed with 5 ml Ultima Gold scintillation cocktail (Packard, Downers Grove, Ill.) and counted in a Beckman LS-8000 liquid scintillation counter. Elution volume is given relative to the first appearance of hemoglobin (void volume) which occurred at 28.4 ml.

Carbohydrate standards employed in gel filtration analysis

The P4 column was calibrated with carbohydrate standards that were obtained as follows. [$^3$H]-Sialic acid was obtained by sialidase treatment (*Arthrobacter ureafaciens*, Calbiochem, La Jolla, Calif.; 0.3 units per ml, pH 5.5, 30 min, 37° C.) of GlyCAM-1 metabolically labeled with [$^3$H]-glucosamine. N-Acetylglucosamine-3-sulfate (GlcNAc-3S, sodium salt) and galactose-6-sulfate (Gal-6S, sodium salt) were from Sigma. Glucuronic acid monosulfate (GlcU-S, mixture of isomers) was prepared by treatment of glucuronic acid with two molar equivalents of $SO_3$-trimethylamine (Westerduin, P., Willems, H. A., and van Boekel, C. A. A., *Tetrahedron Lett.*, 31:6915–6918 (1990)) in anhydrous DMF (4 h, 25° C.) under an inert atmosphere. The reaction was neutralized with saturated $NaHCO_3$ and the product was purified by chromatography on DEAE-Sephadex (Aldrich) eluting with a linear gradient of 0–2M pyridine-acetate (pH 5.4). The pyridinium salt was converted to the sodium salt by passage over Bio-Rad 50W-X-4 resin ($Na^+$ form). Galactose-disulfate and galactose-trisulfate (mixtures of isomers) were prepared by treatment of galactose with five molar equivalents of $SO_3$-trimethylamine in anhydrous DMF (6 h, 40° C.), followed by neutralization with saturated $NaHCO_3$. The products were purified by anion exchange chromatography, and the resulting pyridinium salts were converted to the corresponding sodium salts as described above. All three synthetic derivatives were characterized by negative fast atom bombardment ($FAB^-$) mass spectrometry. GlcNAc-3S was detected in the fractions eluted from the P4 column with the Elson Morgan reaction (Reissig, J. L., Strominger, J. L., and Leloir, L. F., *J. Biol. Chem.*, 217:959–966 (1955)). The galactose-sulfates were detected with the phenol-sulfuric acid assay (Dubois, M., Gilles, K. A., Hamilton, J. K., Rebers, P. A., and Smith, F., *Anal. Chem.*, 28:350–356 (1956)). GlcU-S was detected with the carbazole reaction (Bitter, T., and Muir, H. M., *Anal. Biochem.*, 4:330–334 (1956)).

Anion-exchange chromatography of P4-included fraction of mild acid hydrolysate

The fractions eluting from the P4 column after 42 ml (after 35 ml for ([$^3$H]-GlcN)-labeled GlyCAM-1) were pooled and lyophilized. The residue was dissolved in 200 μl of water and loaded onto a DEAE-Sepharose column (Sigma, acetate form, 80 mm×5 mm, bed volume=1.6 ml) equilibrated with 2 mM pyridine-acetate (pH 5.0). The column was eluted with 8.5 ml of 2 mM pyridine-acetate, followed by 85 ml of a 2–1000 mM linear gradient of pyridine-acetate (pH 5.0). Fractions (30-drops, ≈0.85 ml) were collected and a 30 μl sample of each fraction was counted as above. The column was calibrated with the indicated standards. Fractions eluting from the DEAE-Sepharose column between 50 and 150 mM pyridine-acetate (singly charged material) were pooled and lyophilized.

Gel filtration of singly charged fraction

The preparation of single charged fragments obtained above was redissolved in 200 μl of water and fractionated by gel filtration on the P4 column. Fractions were pooled as follows: peak I (55–60 ml), peak II (49–54 ml), peak III (43–48 ml), and peak IV (36–42 ml). Pooled fractions were lyophilized and the residues were redissolved in 20 μl of water and stored at –80° C. until further analysis.

Total hydrolysis of sulfated carbohydrates

Hydrolysis of the sulfated carbohydrates to yield desulfated and deacetylated monosaccharide units was accomplished by heating samples of peaks I, II and III in 6M HCl 4 h, 100° C.). After hydrolysis, samples were evaporated repeatedly from water and redissolved in water for monosaccharide compositional analysis by high pH anion exchange chromatography (HPAEC).

Desulfation

Peaks II and III were desulfated (without concomitant deacetylation) by incubation in 50 mM methanolic HCl/5% $H_2O$ (24 h, 36° C.). After desulfation, the residues were concentrated, redissolved in water, and loaded onto a DEAE-Sepharose column (80 mm×5 mm, bed volume=1.6 ml) equilibrated in 2 mM pyridine-acetate (pH 5.0). The column was eluted with 2 mM pyridine-acetate (pH 5.0) and uncharged material was recovered as the flow-through fraction. The unbound products were lyophilized and redissolved in water for further analysis.

β-Galactosidase digestions

Radiolabeled oligosaccharide fragments were reacted with jack bean exo-β-galactosidase (0.25 units/ml, Sigma) in 20 mM $NaH_2PO_4$ (buffered to pH 3.5 with acetic acid) in a final volume of 50 μl for 18 h at 37° C. The digests were then subjected to analysis by HPAEC.

Partial hydrolysis of ($^{35}SO_4$)-labeled peak III

The material from $^{35}SO_4$-labeled peak III was reacted with 0.1M $H_2SO_4$ in a final volume of 10 μl (overlayed with mineral oil) for 1 h at 100° C. After neutralization with 2N $NH_4OH$, the hydrolysate was analyzed by HPAEC.

High pH anion exchange chromatography (HPAEC)

Peaks I, II and III and their respective products of desulfation, enzymatic digestion, and hydrolysis were analyzed by HPAEC using a Carbopac PA1 column (Dionex, Sunnyvale, Calif., 250 mm×4 mm). Each sample was injected in 25 μl of water. Elution conditions (flow rate 1 ml/min) were as follows. For analysis of total hydrolysates and desulfated peak II: 20 mM NaOH isocratic; for desulfated peak III and its β-galactosidase digest: 100 mM NaOH isocratic; for sulfated peak II: 150 mM NaOH for 4 min, followed by a linear gradient of 0–250 mM NaOAc in 150 mM NaOH over 20 min (program 1); for sulfated peak I, peak III, β-galactosidase digest and partial hydrolysate of peak III: 50 mM NaOAc in 150 mM NaOH for 5 min, followed by a linear gradient of 50–850 mM NaOAc in 150 mM NaOH over 30 min (program 2). Standards were used at 0.4 mM and analyzed with pulsed amperometric detection. Radiolabeled products were detected by collecting 0.5 min fractions followed by liquid scintillation analysis as described above.

Carbohydrate standards employed in HPLC analysis

Gal-6S, GlcNAc-3S, GlcNAc, Galβ1→3GlcNAc, Galβ1→4GlcNAc (N-acetyllactosamine, LacNAC), and Galβ1→6GlcNAc were from Sigma. Gal-4S and GlcNAc-6S were from V-Labs (Covington, La.). Gal-3S was obtained by hydrolysis of bovine sulfatides (Matreya Inc., Pleasant Gap, Pa.) in 0.1M $H_2SO_4$ (30 min, 100° C.). Gal-2S was synthesized from 12,3,4,6-tetra-O-acetyl-α-D-galactropyranose (Helferich, B., and Zimer, J., Ber., 2604–2611 (1962)) using a procedure based on that of Peat et al. (Peat, S., Bowker, D. M., and Turvey, J. R., Carbohydr. Res., 7:225–231 (1968)). The product was characterized by $^1$H NMR spectroscopy and by FAB$^-$ mass spectrometry. Neutral monosaccharide standards (an equimolar mixture of Fuc, GalN, GlcN, Gal, Glc, and Man) were from Dionex.

The above examples 1–3 demonstrate that the presence of sulfate on GlyCAM-1 is essential for its avid interaction with L-selectin. Example 4 particularly identifies the sulfate modifications of GlyCAM-1. Since conventional analysis of the GlyCAM-1 carbohydrates has so far been hampered by the limited quantities of available ligand, we employed radioactive tracer techniques that have been used widely in the sequencing of glycoprotein oligosaccharides (Varki, A., FASEB J., 5:226–235 (1991); Cummings, R. D., Merkle, R. K., and Stults, N. L., Meth. Cell Biol., 32:141–183 (1989); Shilatifard, A., Merkle, R. K., Helland, D. E., Welles, J. L., Haseltine, W. A., and Cummings, R. D., J. Virol., 67:943–952 (1993); Maemura, K., and Fukuda, M., J. Biol. Chem., 267:24379–24386 (1992)). The oligosaccharides of GlyCAM-1 were metabolically labeled in organ culture with $^{35}SO_4$ and a panel of tritiated carbohydrate precursors to allow specific introduction of label into defined monosaccharide units. The analysis relied on the use of hydrolysis conditions that released sulfated oligosaccharides without the significant cleavage of sulfate esters.

In light of the previously demonstrated ligand activity of fucoidin and egg jelly coat fucan (fucose-4-sulfate rich polysaccharides) for L-selectin (Stoolman, L. M., and Rosen, S. D., J. Cell Biol., 96:722–729 (1983); Imai, Y., True, D. D., Singer, M. S., and Rosen, S. D., J. Cell Biol., 111:1225–1232 (1990)), we initially suspected that sulfated fucose might be present in GlyCAM-1. Prior work has shown that mild acid hydrolysis (0.15M $H_2SO_4$, 30 min, 100° C.) liberates sulfated fucose (fucose-3-sulfate and fucose-3,4-disulfate) from a sea cucumber chondroitin sulfate (Viera, R. P., Mulloy, B., and Mourao, P.A.S., J. Biol. Chem., 266:13530–13536 (1991)). However, hydrolysis of GlyCAM-1 under these conditions released all of the [$^3$H]-Man or [$^3$H]-Fuc labeled counts as neutral fucose, arguing against sulfation of fucose residues in this ligand. The [2-$^3$H]-mannose precursor is known to be incorporated into glycoproteins both as mannose and fucose units (Varki, A., FASEB J., 5:226–235 (1991)). The exclusive incorporation of all mannose label into GlyCAM-1 as fucose indicates the complete absence of mannose in the GlyCAM-1 carbohydrates. This result further substantiates that the oligosaccharide chains of GlyCAM-1 are all O-linked, as previously indicated by the complete resistance of the ligand to N-glycanase digestion (Imai, Y., Singer, M. S., Fennie, C., Lasky, L. A., and Rosen, S. D., J. Cell Biol., 113:1213–1221 (1991)).

Mild acid hydrolysis of ($^{35}SO_4$)-labeled GlyCAM-1 yielded fragments with a hererogenous range of size and charge. We concentrated our analysis on P4-included fractions carrying a single charge.

The structural identification of the singly charged hydrolysis products was accomplished as follows. Fragments labeled with $^{35}SO_4$ and $^3$H-sugars were subjected to further hydrolysis, desulfation, and enzymatic digestion to characterize the monosaccharide components. Sulfate ester linkage positions were assigned by HPAEC analysis with authentic standards. The results of Example 4 identified -$O_3$SO-6-Gal, GlcNAc-6-$OSO_3$-, Galβ1→4GlcNAc-6-$OSO_3$- and -$O_3$SO-6-Galβ1→4GlcNAc as components of GlyCAM-1. The results provide no evidence for the presence of galactose-3-sulfate on GlyCAM-1, although various Gal-3S containing carbohydrates have ligand activity for L-selectin (Green, P. J., Tamatani, T., Watanabe, T., Miyasaka, M., Hasegawa, A., Kiso, M., Yuen, C. T., Stoll, M. S., and Feizi, T., Biochem. Biophys. Res. Commun., 188:244–251 (1992); Suzuki, Y., Toda, Y., Tamatani, T., Watanabe, T., Suzuki, T., Nakao, T., Murase, K., Kiso, M., Hasegawa, A., Tadano-Aritomi, K., Ishizuka, I., and Miyasaka, M., Biochem. Biophys. Res. Commun., 190:426–434 (1993)). GlcNAc-6S has been identified in a wide assortment of glycoconjugates which include the glycosaminoglycan chains of keratan sulfate (Rodén, L., In The Biochemistry of Glycoproteins and Proteoglycans, p. 267–372 (1980) (W. J. Lennarz, ed.) Plenum Press: New York), viral envelope glycoproteins of type I human immunodeficiency virus (Shilatifard, A., Merkle, R. K., Helland, D. E., Welles, J. L., Haseltine, W. A., and Cummings, R. D., J. Virol., 67:943–952 (1993), chicken adipose lipoprotein, glycoproteins of bovine large vessel endothelial cells (Roux, L., Holojda, S., Sundblad, G., Freeze, H. H., and Varki, A., J. Biol. Chem., 263:8879–8889 (1988)), bovine and human thyroglobulin (Spiro, R. G., and Bhoyroo, V. D., J. Biol. Chem., 263:14351–14358 (1988), and a rhizobial nodulation factor (Roche, P., Debellé, F., Maillet, F., Lerouge, P., Faucher, C., Truchet, G., Dénarié, J., and Promé, J. C., Cell, 67:1131–1143 (1991)). Gal-6S has been found in keratan sulfates (Rodén, L., In The Biochemistry of Glycoproteins and Proteoglycans, p. 267–372 (W. J. Lennarz, ed.) Plenum Press: New York (1980)), human tracheobronchial mucins (Mawhinney, T. P., Adelstein, E., Morris, D. A., Mawhinney, A. M., and Barbero, G. J., J. Biol. Chem., 267:2994–3001 (1986), rat salivary mucins together with GlcNAc-6S (Slomiany, B. L., Piotrowski, J., Nishikawa, H., and Slomiany, A., Biochem. Biophys. Res. Commun., 157:61–67 (1988) and recombinant human tissue plasminogen activator (Pfeiffer, G., Stirm, S., Geyer, G., Strube, K.-H., Bergwerff, A. A., Kamerling, J. P., and Vliegenthart, J. F. P., Glycobiology, 2:411–418 (1992). In keratan sulfate and plasminogen activator, Gal-6S occurs on N-acetyllactosamine units, as is the case for the structures identified in Example 4.

The functional requirements for sialic acid, sulfate and probably fucose must be included in any model for the recognition determinants on GlyCAM-1. One possibility is that individual O-linked chains contain either sialic acid-based or sulfate-based determinants. The individual chains would be recognized by separate lectin domains of oligomeric L-selectin or may form a combined epitope for a single lectin domain (Norgard, K. E., Moore, K. L., Diaz, S., Stults, N. L., Ushiyama, S., McEver, R. P., Cummings, R. D., and Varki, A., *J. Biol. Chem.*, 268:12764–12774 (1993)). Removal of either sialic acid or sulfate would greatly reduce the overall avidity of the interaction between the ligand and L-selectin.

Preferred ligands have sulfation and sialylation on the same O-linked chain forming an L-selectin recognition site, e.g. as a sulfated sLe$^x$-like structure. Previously, we observed that all ($^{35}SO_4$)-labeled O-linked chains released from GlyCAM-1 by beta elimination are able to bind to a sialic acid-specific lectin (Limax agglutinin) (Imai, Y., and Rosen, S. D., *Glycoconjugate J.*, 10:34–39 (1993)). Thus, sulfation does not occur without sialylation on individual chains.

Example 5

Analysis of hydrolysis fragments of metabolically-labeled GlyCAM-1

GlyCAM-1 was metabolically labeled in lymph node organ culture with $^{35}SO_4$, and a panel of tritiated carbohydrate precursors as described in Example 1 above. Mild hydrolysis conditions were used that released sulfated oligosaccharides without the generation of free sulfate. Low molecular weight and singly-charged fragments, obtained by a combination of gel filtration and anion exchange chromatography, were analyzed. The identification of the fragments relied on the use of a variety of radiolabeled sugar precursors (R. D. Cummings, R. K. Merkle and N. L. Stults, in *Methods in Cell Biology* (Academic Press, 1989), vol. 32, and A. Varki, *FASEB J.*, 5:226–235 (1991)) and subjected the singly charged fractions to further chemical and enzymatic hydrolysis with the eventual assignment of structures by high pH anion exchange chromatography analysis with authentic standards. The sulfated constituents of GlyCAM-1 were identified as -O$_3$SO-6-Gal, GlcNAc-6-OSO$_3$, Galβ1→4GlcNAc-6-OSO$_3$- and -O$_3$SO-6-Galβ1→4GlcNAc.

Example 6

Reactivity of GlyCAM-1 with lectins

Previous work has established that sulfate (Y. Imai, L. A. Lasky and S. D. Rosen, *Nature*, 361:555–557 (1993)) and sialic acid and probably fucose (Y. Imai, L. A. Lasky and S. D. Rosen, *Glycobiology*, 4:373–381 (1992)) are essential for the avid interaction of GlyCAM-1 with L-selectin. GlyCAM-1 was analyzed with respect to sialic acid and fucose substitutions of the sulfated structures obtained in the hydrolysis of GlyCAM-1 (see Example 5 above). For this purpose, a group of lectins with defined carbohydrate specificity was used to examine their binding to GlyCAM-1. Both normal and undersulfated GlyCAM-1 with or without enzymatic desialylation and/or defucosylation was tested.

($^3$H-Gal)-labeled GlyCAM-1 was produced in mouse lymph node organ cultures as described in Examples 1–4 above. Undersulfated GlyCAM was generated by organ culture of murine lymph nodes in medium containing 10 mM Na-chlorate, a known inhibitor of sulfation. GlyCAM-1 was isolated from the conditioned media by immunoprecipitation with an antibody to a peptide sequence in the core protein of GlyCAM-1 (CAM02 Ab), as described in Examples 1–4 above. While GlyCAM incorporated about the same [$^3$H]-galactose activity in the presence or absence of chlorate (2×10$^6$ cpm from 0.25 mCi input), the incorporation of [$^{35}$S]-sulfate was suppressed in the presence of chlorate to 10% of that in the control (0.16×10$^6$ vs. 1.75×10$^6$ cpm, 0.5 mCi input). Desialylation of GlyCAM-1 was accomplished in all cases by treatment with *Arthrobacter ureafacens* sialidase (1.75 units/ml) in 120 mM Na acetate, pH 5.5 (18 h 37° C.).

The lectins used in the analysis were as follows:

WGA: wheat germ agglutinin (H. Lis and N. Sharon, *Ann Rev Biochem*, 55:35–67 (1986)); recognizes sialic acid (Sia) and terminal GlcNAc,. eluant: GlcNAc AAA: *Aleuria aurantia* agglutinin (H. Debray and J. Montreuil, *Carbo. Res.*, 185:15–20 (1989)); recognizes α1-2, α1-3, and α1-6 linked fucose, eluant: fucose TJA-1: *Trichosanthes japonica* agglutinin (K. Yamashita, K. Umetsu, T. Suzuki and T. Ohkura, *Biochemistry*, 31:11647–50 (1992)) recognizes Siaα2-6Galβ1→4GlcNAc or SO$_4$-6-Galβ1-4GlcNAc. eluant: lactose SNA: *Sambucus nigra* (elderberry bark) agglutinin (K. Yamashita, K. Umetsu, T. Suzuki and T. Ohkura, *Biochemistry*, 31:11647–50 (1992), and N. Shibuya et al., *J. Biol Chem.*, 262:1569–1601 (1987)); recognizes Siaα2-6GalNAc, Siaα2-6-Galβ1-4GlcNAc and SO$_4$-6-Galβ1-4GlcNAc. eluant: lactose MAA: *Macckia amurensis* agglutinin (R. N. Knibbs, I. J. Goldstein, R. M. Ratcliffe and N. Shibuya, *J. Biol Chem.*, 266:83–88 (1991)); recognizes Siaα2-3Galβ1-4GlcNAc. eluant: lactose PNA: peanut agglutinin (H. Lis and N. Sharon, *Ann Rev Biochem.*, 55, 35–67 (1986)); recognizes Galβ1-3-GalNAc. eluant: lactose.

LEA: *Lycopersicon esculentum* agglutinin (tomato lectin) (R. D. Cummings, R. K. Merkle and N. L. Stults, in *Methods in Cell Biology* (Academic Press, 1989), vol. 32,); binds to (β1-4GlcNAc) oligomers with no requirement that GlcNAc is consecutive. Eluant: N-acetylglucosamine. *Sugar abbreviations used above: Fuc, fucose; Gal, galactose; GalNAc, N-acetylgalactosamine; GlcNAc, N-acetylglucosamine; Sia, sialic acid (encompasses all naturally occurring variants of this sugar).

As an additional precipitating reagent, an antibody to the C-terminal peptide of GlyCAM-1 (CAM05 Ab) was also used. The eluant for CAM05 Ab was 0.1M glycine-HCl, 0.2M NaCl, 0.25% Triton X-100, pH 3.0. Binding was expressed as % of total cpm input.

GlyCAM-1 preparations were agitated with immobilized lectin (0.2 ml matrix gel per ml, derivatization: 1–2 mg lectin per ml gel) in phosphate buffered saline (PBS) containing 0.1% BSA 0.01% NaN$_3$ for 2 hr at 4° C., then matrices were centrifuged, washed four times with PBS containing 0.25% Triton X-100 and eluted with 100 mM specific eluant in PBS containing 0.25% Triton X-100. The activity in the eluates was then determined by liquid scintillation counting.

The results of the lectin precipitation analysis were as shown in Table I below.

TABLE I

Lectin Precipitation Analysis

| | | % of CPM Precipitated | | | | | | CAM05 |
|---|---|---|---|---|---|---|---|---|
| Presence of | | | | | | | | |
| Sia | $SO_4$ | TJA-1 | SNA | MAA | WGA | AAA | PNA | Ab |
| + | + | 8.2 | 11.2 | 4.2 | 86.7 | 61.5 | 1.5 | 58.7 |
| + | − | 1.6 | 3.6 | 28.9 | 82.8 | 81.2 | 2.9 | 88.8 |
| − | + | 63.0 | 35.0 | 0.2 | 14.1 | 64.0 | 20.8 | 73.3 |
| − | − | 3.1 | 0.2 | 0.4 | 24.3 | 69.5 | 38.9 | 85.5 |

The results of the above experiments on lectin precipitation demonstrated:

(a) Desialylation with *Arthrobacter sialidase* exposed a cryptic binding site for both TJA-1 and SNA. This site depended on sulfation since the desialylated and undersulfated material failed to bind to these two lectins.

(b) Undersulfation of GlyCAM-1 exposed a cryptic MAA-binding activity, which depended on sialylation.

(c) Desialylation exposed a cryptic PNA-binding activity. Binding to PNA was not markedly influenced by presence or absence of sulfate.

The hydrolysis analysis of metabolically labeled GlyCAM-1 together with the lectin precipitation analysis strongly supported that

Siaα2-3(SO$_4$-6)Galβ1-4GlcNAc was present within a major capping structure for GlyCAM-1 carbohydrate chains. The results with PNA suggested that the GlyCAM-1 carbohydrates contained a sialylated T-antigen like structure (i.e., Siaα2-3Galβ1-3GalNAc).

Example 7

Sequential exoglycosidase digestion of GlyCAM-1

Normal or undersulfated GlyCAM-1, labeled with [$^3$H]-Gal, was isolated from conditioned medium of lymph nodes by immunoprecipitation with CAM02 Ab conjugated to protein A-agarose as described above. The isolated ligand was digested, with or without prior desialylation, with the following enzymes:

(1) exo-β1-4galactosidase (from Diplococcus, Boehringer Mannheim, #1088718) at 0.1 units/ml in 50 mM Na-cacodylate pH 6.0 for 48 h at 37° C.; or (2) exo-β1-4 galactosidase (from Diplococcus, Boehringer Mannheim, #1088718) at 0.1 units/ml plus α1-¾ fucosidase (Takara Biochemicals, Tokyo) (K. Maemura and M. Fukuda, *J Biol Chem.*, 267:24379–24386 (1992)) at 0.1 milliunits/ml in 50 mM Na-cacodylate pH 6.0 for 48 h at 37° C.

The digests were loaded on Sephadex G-25 gel filtration columns (270 mm×8 mm in PBS, 0.25% Triton X-100). Columns were eluted with PBS, 0.25% Triton X-100 and 0.5 ml fractions were collected. Entire fractions were counted for [$^3$H]-radioactivity. The undigested material eluted in the void volume (4–5 ml) while liberated [$^3$H]-Gal was included in the column and eluted 2.5–4 ml after the void volume.

The results with [$^3$H]-Gal were as shown in Table II below.

TABLE II

Digestion of [$^3$H] Gal. Labelled GlyCAM-1

| | | Percent Release of [$^3$H] Gal. Labelled by GlyCAM-1 | |
|---|---|---|---|
| Presence of | | | Exo β1-Gal-ase + |
| Sia | $SO_4$ | Exo β-Gal-ase | Exo α1¾ Fuc-ase |
| + | + | 0 | 0 |
| + | − | 0 | 0 |
| − | + | 4 | 12 |
| − | − | 10 | 35 |

Normal or undersulfated GlyCAM-1, metabolically labeled with [$^3$H]-fucose was digested with α1-¾ fucosidase (Takara Biochemicals, Tokyo) at 0.1 milliunits/ml in 50 mM Na-cacodylate, with or without concomitant desialylation. Liberated [$^3$H]-Fuc was determined by gel filtration analysis as described above for galactose. The results with [$^3$H]-Fuc were as shown in Table III below.

TABLE III

Digestion of [$^3$H]-fucose labelled GlyCAM-1

| Presence of | | Percent Release of [$^3$H]-Fuc from |
|---|---|---|
| Sia | $SO_4$ | GlyCAM-1 by α1¾ fucosidase |
| + | + | 0 |
| + | − | 0 |
| − | + | 70 |
| − | − | 85 |

The ability of desialylated ([$^3$H]-Gal)-labeled GlyCAM-1, undersulfated or normal, with or without treatment with the α1-¾ fucosidase to bind to AAA or LEA (tomato lectin) was determined. See Example 6 above for the binding specificity of AAA and LEA and for the assay conditions.

The results of the analysis were as shown in Table IV below.

TABLE IV

Binding of ([$^3$H]-GAL)-GlyCAM-1

| Presence of | | | Percent Binding of ([$^3$H])-Gal)-GlyCAM-1 | |
|---|---|---|---|---|
| Sia | Fucose | $SO_4$ | AAA | LEA |
| − | + | + | 60 | 5.2 ± 0.2 |
| − | + | − | 80 | 13.9 ± 0.4 |
| − | − | + | 23.4 | 47.6 ± 3.7 |
| − | − | − | 10.1 | 43.8 ± 1.8 |

The results of experiments in Tables II, III and IV demonstrated the following:

1. About 35% of all galactose in GlyCAM-1 was in a penultimate position relative to sialic acid and was linked β1→4 to GlcNAc. This result followed from the fact that undersulfated, desialylated and defucosylated material released 35% of its [$^3$H]-Gal counts upon treatment with β1-4 exo-galactosidase (Table II). All of this galactose was normally sialylated, judging from the complete lack of activity of β1-4 exo-galactosidase on GlyCAM-1 unless the ligand was desialylated. This was true whether or not the molecule was undersulfated.

2. Fucose is α1→3 linked to GlcNAc. This result followed from the actions of the α1-¾ fucosidase which: (1)

accentuated the release of [$^3$H]-Gal counts from GlyCAM-1 by β1-4 exo-galactosidase (Table II); (2) directly released [$^3$H]-Fuc counts from GlyCAM-1 (Table III); and (3) increased the binding of GlyCAM-1 to LEA, which is known to bind to β1-4 linked GlcNAc (Table IV). Since the 4-position of GlcNAc is involved in the linkage to Gal (i.e., Galβ1-4GlcNAc), fucose must be bound in a α1-3 linkage to GlcNAc. From the data of Table II, it was estimated that ≈70% of the first GlcNAc was substituted with fucose.

3. The presence of sulfation greatly hindered the release of [$^3$H]-Gal counts from GlyCAM-1 upon treatment with β1-4 exo-galactosidase (Table II). This result provided further evidence with the β1-4 linked galactose residues were substituted with sulfate, probably at the 6-position. From the effect of exo-β-galactosidase on the release of [$^3$H]-Gal counts from defucosylated, sulfated GlyCAM-1 vs. defucosylated, undersulfated GlyCAM-1, it was estimated that ≈60% of the terminal β1-4 galactose residues were substituted with sulfate.

Proposed structure for capping groups of GlyCAM-1 carbohydrate:

The data presented above on the analysis of hydrolysis products of metabolically labeled GlyCAM-1, binding of GlyCAM-1 to lectins of defined carbohydrate specificity, and the use of glycosidases to degrade the oligosaccharide chains of GlyCAM-1 demonstrated that a typical carbohydrate chain of GlyCAM-1 consisted of a sialylated T antigen of formula II below, i.e. Siaα2-3Galβ1-3GalNAc-O-Ser/Thr that was extended at the 6-position of the Ser/Thr-linked GalNAc with an unknown number of N-acetyllactosamine units, which were capped at the nonreducing terminus by a 6-sulfated, sialyl Lewis X structure (i.e., terminal galactose substituted by both α2-3 linked sialic acid and sulfation at the 6-position.

Example 8

Experiments were conducted to determine the binding of GlyCAM and CD34 to antibody MECA-79 m Ab. Streeter, P. R., Rouse, B. T. N., and Butcher, E. C., *J. Cell Biol.*, 107:1853–1862 (1988); Michie, S. A., Streeter, P. R., Bolt, P. A., Butcher, E. C., and Picker, L. J., *Amer. J. Path.* 143:1688–1698 (1993). Results of these experiments demonstrated that binding of GlyCAM and CD34 to MECA-79 m Ab depends on the sulfation of these ligands.

The above experiments show that sulfation at particular positions of saccharide molecules is important with respect to the binding of selectin ligands to selectin receptors. Specifically, the above results demonstrate that the sulfate moiety is present at the 6-position on saccharide molecules present within naturally occurring selectin ligands. Specifically, the sulfate is present at the 6-position of N-acetylglucosamine and at the 6-position of galactose. Accordingly, the above experiments demonstrate that, by inhibiting sulfation, one can interrupt the biochemical process which contributes to inflammation when the process occurs at an unacceptably high rate. Further, by removing the sulfate moiety, one can, in a similar manner, inhibit the biochemical processing which can, and often does, result in inflammation.

The various aspects of the present invention have been shown and described herein in what is considered to be the most practical, and preferred embodiments. It is recognized, however, that departures may be made therefrom which are within the scope of the invention, and that obvious modifications will occur to one skilled in the art upon reading this disclosure.

We claim:

1. A method of treating inflammation resulting from the binding of L-selectin to a sulfated L-selectin ligand, comprising:

administering to a patient in need thereof a therapeutically effective amount of a sulfatase enzyme in a pharmaceutically acceptable carrier; and allowing the sulfatase enzyme to remove a sulfate moiety from a saccharide molecule of a naturally occurring L-selectin ligand.

2. The method as claimed in claim 1, wherein the sulfatase enzyme is selected from the group consisting of galactose-6-sulfate sulfatase and N-acetyl-glucosamine-6-sulfate sulfatase.

3. The method as claimed in claim 2, wherein the sulfatase enzyme is galactose-6-sulfate sulfatase.

4. The method as claimed in claim 1, wherein the administering is by I.V.

5. The method of claim 1, wherein the sulfatase enzyme is administered in an amount in the range of 100 mg to about 5 grams.

6. The method of claim 1, wherein the sulfatase enzyme is administered in an amount of from 1 to 10 units per 70 kg of patient body weight.

* * * * *